United States Patent
Ohrn

(10) Patent No.: US 10,832,794 B2
(45) Date of Patent: Nov. 10, 2020

(54) SYSTEM FOR MOLECULAR PACKING CALCULATIONS

(75) Inventor: Anders Ohrn, Vancouver (CA)

(73) Assignee: ZYMEWORKS INC., Vancouver (CA)

( * ) Notice: Subject to any disclaimer, the term of this patent is extended or adjusted under 35 U.S.C. 154(b) by 1103 days.

(21) Appl. No.: 13/822,258

(22) PCT Filed: Sep. 22, 2011

(86) PCT No.: PCT/CA2011/001061
§ 371 (c)(1),
(2), (4) Date: May 28, 2013

(87) PCT Pub. No.: WO2012/037659
PCT Pub. Date: Mar. 29, 2012

(65) Prior Publication Data
US 2013/0238299 A1    Sep. 12, 2013

Related U.S. Application Data

(60) Provisional application No. 61/386,406, filed on Sep. 24, 2010.

(51) Int. Cl.
| | | |
|---|---|---|
| G01N 33/48 | (2006.01) | |
| G16B 5/00 | (2019.01) | |
| G01N 33/531 | (2006.01) | |
| G01N 33/68 | (2006.01) | |
| G16B 15/00 | (2019.01) | |
| G06G 7/58 | (2006.01) | |

(52) U.S. Cl.
CPC .............. G16B 5/00 (2019.02); G01N 33/531 (2013.01); G01N 33/68 (2013.01); G16B 15/00 (2019.02); G01N 2500/00 (2013.01)

(58) Field of Classification Search
None
See application file for complete search history.

(56) References Cited

U.S. PATENT DOCUMENTS

| | | |
|---|---|---|
| 5,241,470 A | 8/1993 | Lee et al. |
| 2013/0238299 A1 | 9/2013 | Ohrn |

FOREIGN PATENT DOCUMENTS

| | | |
|---|---|---|
| WO | WO 1993/014465 | 7/1993 |
| WO | WO 2008/071540 | 6/2008 |
| WO | WO 2012/037659 A1 | 3/2012 |

OTHER PUBLICATIONS

Betancourt, M., "Efficient Monte Carlo trial moves for polypeptide simulations" *The Journal of Chemical Physics*, vol. 123 (2005).
Chowdry, A. et al., "An Object-Oriented Library for Computational Protein Design" *Journal of Computational Chemistry*, vol. 28, No. 14, pp. 2378-2388 (2007).
Douguet, D. et al., "DOCKGROUND resource for studying protein-protein interfaces" *Structural bioinformatics*, vol. 22, No. 21, pp. 2612-2618 (2006).
Edelsbrunner, H. and Koehl, P., "The Geometry of Biomolecular Solvation" *Discrete and Computational Geometry*, MSRI Publications, vol. 52, pp. 241-273 (2005).
Fleming, P. and Richards, F., "Protein Packing: Dependence on Protein Size, Secondary Structure and Amino Acid Composition" *J. Mol. Biol.*, vol. 299, pp. 487-498 (2000).
Gao, Y. et al., "DOCKGROUND system of databases for protein recognition studies: Unbound structures for docking" *Proteins*, vol. 69, pp. 845-851 (2007).
Liu, L., "BEST: Bayesian estimation of species trees under the coalescent model" *Phylogenetics*, vol. 24, No. 21, pp. 2542-2543 (2008).
Metropolis, N. et al., "Equation of State Calculations by Fast Computing Machines" *The Journal of Chemical Physics*, vol. 21, No. 6, pp. 1087-1092 (1953).
Pattabiraman, N. et al., "Occluded Molecular Surface: Analysis of Protein Packing" Journal of Molecular Recognition, vol. 8, pp. 334-344 (1995).

*Primary Examiner* — Eric S DeJong
(74) *Attorney, Agent, or Firm* — Morgan, Lewis & Bockius LLP; Brett Lovejoy

(57) ABSTRACT

The invention provides a computer implemented method of quantifying the quality of packing for a residue comprising one or more residue atoms in a first protein in a first conformation, the method comprising: (a) calculating one or more close contact potentials based on a distance between the one or more residue atoms and one or more environment atoms, (b) calculating a contact area of the one or more residue atoms that is exposed to the one or more environment atoms and (c) calculating a close contact surface density (CCSD) by dividing the sum of the one or more close contact potentials by the contact area.

9 Claims, 18 Drawing Sheets

SYSTEM FOR MOLECULAR PACKING CALCULATIONS

CROSS-REFERENCE TO RELATED APPLICATIONS

This application claims priority to U.S. Application No. 61/386,406, filed Sep. 24, 2010, which is incorporated by reference.

TECHNICAL FIELD

The field of the invention relates to the structural characterization of proteins, in particular the quality of the residue packing in the presence of a continuous solvent, and the computation of the free energy associated with a given structure.

BACKGROUND

The design of "biobetters", or biologicals that have been optimized to serve medical purposes, provides the opportunity for huge advances in human and animal health. Biological molecules are extremely complex, and their structure and activities are governed by multitudinous atomic forces involving structure and milieu.

Others have computed contacts within biologicals, but important information has been ignored in order to achieve calculations without overwhelming computing resources. In one method illustrated in Pattabiraman et al., Journal of Molecular Recognition, 1995, 8: 334, the occluded surface method is basically a weighted relative occluded surface area (meaning not exposed to solvent) for a particular residue. The method begins with the discretization of the total surface area of a given residue. A given surface element is considered occluded when the surface of another protein atom is within 2.8 Å in the direction of the normal vector of the given surface element. The area associated with the occluded surface is weighted by how close the occluding atom is located and added to a sum. The sum is divided by the total surface area of the residue. The weighting of the surface areas makes the sum larger if the occluded surface is well packed. On the other hand, the metric thus obtained characterizes the quality of packing of the entire residue in the environment of other residues, which implies that the metric will become smaller as the solvent exposure of the residue increases.

The methods used in the past, and history, are well reviewed in Fleming and Richards' paper in Journal of Molecular Biology, 2000, 299: 487. The previous methods have achieved a geometric sense of the packing quality in the environment of other residues.

A more informative approach that is more closely related to the relevant thermodynamic properties of binding and stability is required to establish a route to optimized biological drugs.

An improved method of arriving at protein conformational information is therefore needed.

SUMMARY OF INVENTION

The close contact surface density (CCSD) method aims at quantifying how well-packed a certain residue of a protein is in a way that gives quantities that are (1) transferable between different types of residues and (2) related to the contribution of packing to the thermodynamics of a particular process, such as binding or folding. The quality of the packing is considered relative to a reference state where some or all residue-to-residue contacts have been replaced by contacts with the solvent. The CCSD quantity is therefore related to the ubiquitous dispersion interaction (the attractive interaction between atoms), without taking the complex physical dependence into account.

In qualitative terms, the CCSD method enables a user to answer the questions:
1. In the current fold, how well packed is a region compared to the fold where all inter-residue contacts have been replaced by contacts with a continuous solvent?
2. In the current docked configuration, how well packed is a region of the ligand at the interface between the ligand and receptor compared to the apo form of the ligand where all ligand-receptor contacts have been replaced by contacts with a continuous solvent?

Accordingly in one aspect, the invention provides a computer implemented method of quantifying the quality of packing for a residue comprising one or more residue atoms in a first protein in a first conformation, the method comprising: (a) calculating one or more close contact potentials based on a distance between the one or more residue atoms and one or more environment atoms, (b) calculating a contact area of the one or more residue atoms that are exposed to the one or more environment atoms and (c) calculating a close contact surface density (CCSD) by dividing the sum of the one or more close contact potentials by the contact area, wherein the method is performed on a computer system comprising (1) a clock, (2) a memory, and (3) a processor and wherein each step of the method is performed utilizing the processor.

DESCRIPTION OF EMBODIMENTS

Described herein are methods for quantifying residue packing in a protein in various configurations and environments.

In one aspect, the invention provides a computer implemented method of quantifying the quality of packing for a residue comprising one or more residue atoms in a first protein in a first conformation, the method comprising: (a) calculating one or more close contact potentials based on a distance between the one or more residue atoms and one or more environment atoms, (b) calculating a contact area of the one or more residue atoms that are exposed to the one or more environment atoms and (c) calculating a close contact surface density (CCSD) by dividing the sum of the one or more close contact potentials by the contact area. In exemplary embodiments, the method is performed on a computer system comprising (1) a clock, (2) a memory, and (3) a processor, wherein each step of the method is performed utilizing the processor.

Figure 1:
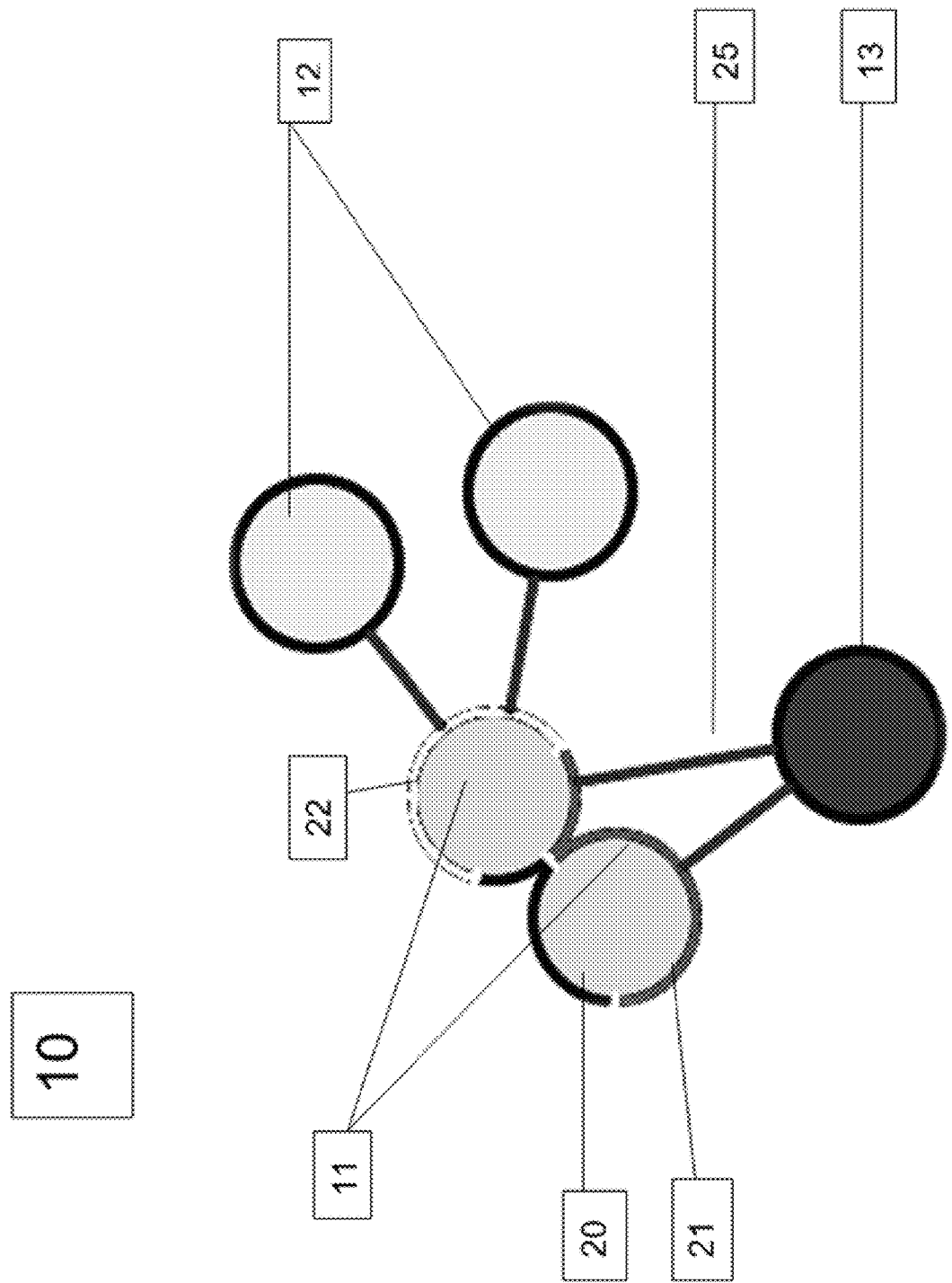
FIG. 1 shows a model of atoms of a test molecule (11, $S_{analyze}$), a ligand (13, $S_{ligand}$) and a receptor (12, $S_{receptor}$) showing lines of contact.

Turning to FIG. 1, let $S_{analyze}$ be the set of test atoms (also referred to herein as "residue atoms") (11) grouped into residues that are to be analyzed with respect to CCSD. Distances can be measured between any of these residue atoms and environment atoms, which are atoms in the vicinity of the residue atoms. Which distances are measured can be determined by the user-defined cutoff described below.

Examples of environment atoms include those that are part of the same molecule as the residue atoms and those that are part of a different molecule. For example, let $S_{ligand}$ be the set of atoms (13) that constitute a ligand or part of a ligand. Let $S_{receptor}$ be the set of atoms (12) that constitute a receptor or part of a receptor, which may be optionally present. The three sets of atoms and their close contacts are illustrated in FIG. 1 at (10). $S_{ligand}$ and $S_{receptor}$ are thus examples of environment atoms. In some embodiments, $S_{analyze}$ is a subset of a receptor. In some embodiments, $S_{analyze}$ is a subset of a ligand.

The terms "receptor" and "ligand" refer generally to any two molecules that bind to each other. In some instances, these terms are interchangeable. A receptor and a ligand can bind to each other to form a complex. In exemplary embodiments, at least one member of a receptor-ligand pair is a protein. In exemplary embodiments, both the receptor and the ligand of a receptor-ligand pair are proteins. In some embodiments, a receptor is a protein. In some embodiments, a ligand is selected from an amino acid, peptide, polypeptide, nucleotide, polynucleotide, saccharide, polysaccharide, lipid and a small molecule (e.g., MW <500 D). In exemplary embodiments, a protein is an antibody or an antigen.

In FIG. 1, atoms (11) $S_{analyze}$ are part of the same residue; atoms (12) are members of $S_{receptor}$; and atom (13) is a member of $S_{ligand}$. The darkness of the shell of the atoms in FIG. 1 indicates the set of atoms to which the shaded surface area is exposed, with darkest black (20) meaning neither ligand nor receptor, mid-range (21) as ligand only, and lightest (22) indicating both ligand and receptor exposure.

The shaded connecting lines (25) indicate separations of less than $r_c$, the distance threshold below which two atoms are considered to be in close contact. The distance $r_c$ can be between various points on the two atoms, for example, from the center of one to the center of the other or from the surface of one to the surface of the other. The distance cut-off is selected based on typical minimum atom-atom separations in proteins. Therefore, in exemplary embodiments, the cutoff should be at or slightly above two times the van der Waals radii of typical protein atoms (e.g., C, N, O, S and H).

Let $N_{lig}$ and $N_{rec}$ be the sum of the close contact potential (vide infra) between all pairs of test atoms and the ligand and receptor atoms, respectively. Let $SA_{lig}$ and $SA_{rec}$ be the surface area of the test atoms exposed to the ligand and receptor, respectively; then ratios $$R_{lig} = \frac{N_{lig}}{SA_{lig}}$$

$$R_{rec} = \frac{N_{rec}}{SA_{rec}}$$

are the CCSDs. In some embodiments, the CCSD is less than about 0.50, 0.45, 0.40, 0.35, 0.30, 0.25, 0.20, 0.15 or 0.10 $\text{Å}^{-2}$. In exemplary embodiments, the CCSD is less than about 0.25 $\text{Å}^{-2}$.

These surface areas can be referred to as "contact areas", with receptor contact area referring to the area on a test residue atom being exposed to a receptor, and ligand contact area referring to the area on a test residue atom being exposed to a ligand. In exemplary embodiments, the analytical method to compute volumes and surfaces described in Edelsbrunner and Koehl, Combinatorial and Computational Geometry, 2005, 52: 243-275 is used. The radius of the probe atom is 1.4 Å. In practical terms, the two mentioned surface areas are computed through these operations:

1. Compute the total solvent accessible surface area of the given residue type in vacuum, SA_tot
2. Compute the solvent accessible surface area of the given residue in the presence of the ligand environment, SASA_lig.
3. Compute the solvent accessible surface area of the given residue in the presence of the ligand and receptor environment (if applicable), SASA_lig+rec
4. Referring to FIG. 1, the following equalities can be formulated:

SA_rec=SASA_lig(20+22)−SASA_lig+rec(20) and
SA_lig=SA_tot(20+21+22)−SASA_lig (20+22).

At most three SASA calculations are needed to compute the two contact surface areas.

The methods comprise calculating one or more close contact potentials. In some embodiments, the close contact potential for two atoms a and b separated by a distance $r_{ab}$ is:

$$U_{ab}(r_{ab}) = \begin{cases} 1 & \text{if } r_{ab} < r_c \\ \frac{1}{d}(r_c - r_{ab}) + 1 & \text{if } r_c < r_{ab} < r_c + d \\ 0 & \text{if } r_{ab} > r_c + d \\ 0 & \text{if } B \end{cases}$$

where d is a small non-zero off-set and rc is a distance cutoff or threshold. This is almost exactly like counting the number of close contacts, except the potential has been made continuous to make the numbers $N_{lig}$ and $N_{rec}$ stable to minor structural perturbations. The symbol B refers to atoms a and b that are either members of the same residue or that are bonded either directly (1-2 bonded), through one intervening atom (1-3 bonded) or through two intervening atoms (1-4 bonded). A typical value of the off-set is about 0.2 Å. Other offsets include about 0.05, 0.1, 0.15, 0.25, 0.3 and 0.35 Å. The criteria to set the off-set can be empirical and based on the range of minor structural perturbations that in the application should be considered irrelevant Other close contact potential known in the art may also be suitable.

In some embodiments, the cutoff $r_c$ is equal to or greater than 2.8 Å. In some embodiments, $r_c$ is equal to or greater than a distance selected from 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 and 5.0 Å. In some embodiments, rc +d is equal to or greater than 2.8 Å. In some embodiments, $r_c$ +d is equal to or greater than a distance selected from 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 and 5.0 Å. In exemplary embodiments, $r_c$ is about 3.6 Å. In exemplary embodiments, $r_c$ +d is about 3.8 Å.

Thus, in exemplary embodiments, the method comprises counting or quantifying the number of close contacts (for example, via a close contact potential) but not the number of close contact atoms. For an atom that is close to several other atoms, the number of close contacts can be different from the number of close contact atoms. For example, the atom (13) in FIG. 1 is close to two atoms in the set of atoms to be analyzed. Hence it adds 2, not 1, to $N_{lig}$.

In exemplary embodiments, the methods are symmetric with respect to the atom sets. For example, if $S_{analyze}$ and $S_{receptor}$ are interchanged in FIG. 1 the number of contacts remains the same, but the number of contact atoms changes. This is also the definition that mostly resembles a pairwise van der Waals potential.

In exemplary embodiments, the method comprises normalizing a CCSD. This can guarantee that CCSD values are comparable between residue types. In exemplary embodiments, a standard score or Z-score is also computed, which is defined as $$Z(x) = \frac{x - \mu}{\sigma}$$

where μ is the average CCSD value for a given residue type, a the standard deviation and x the particular CCSD value. Computing Z serves to translate the "raw" CCSD data. The averages and standard deviations are obtained by computing the CCSD on a large set of benchmark structures (see Tables 1 and 2 in subsequent sections). Normalized CCSDs can be useful for constructing histograms, for example.

The averages and standard deviations are obtained by quadratic interpolation. To summarize, for a given damping parameter and probe radius, the averages and standard deviations are computed for three different close contact cutoffs (e.g., 3.6, 4.0 and 4.5 Å). The averages and standard deviations are found to be slightly non-linear. A quadratic form is fitted to the three points and used to interpolate between the three points. Observe that this construction implies that the averages and standard deviations are exactly right for the cutoff distances equal to the three specific values.

Figure 7:
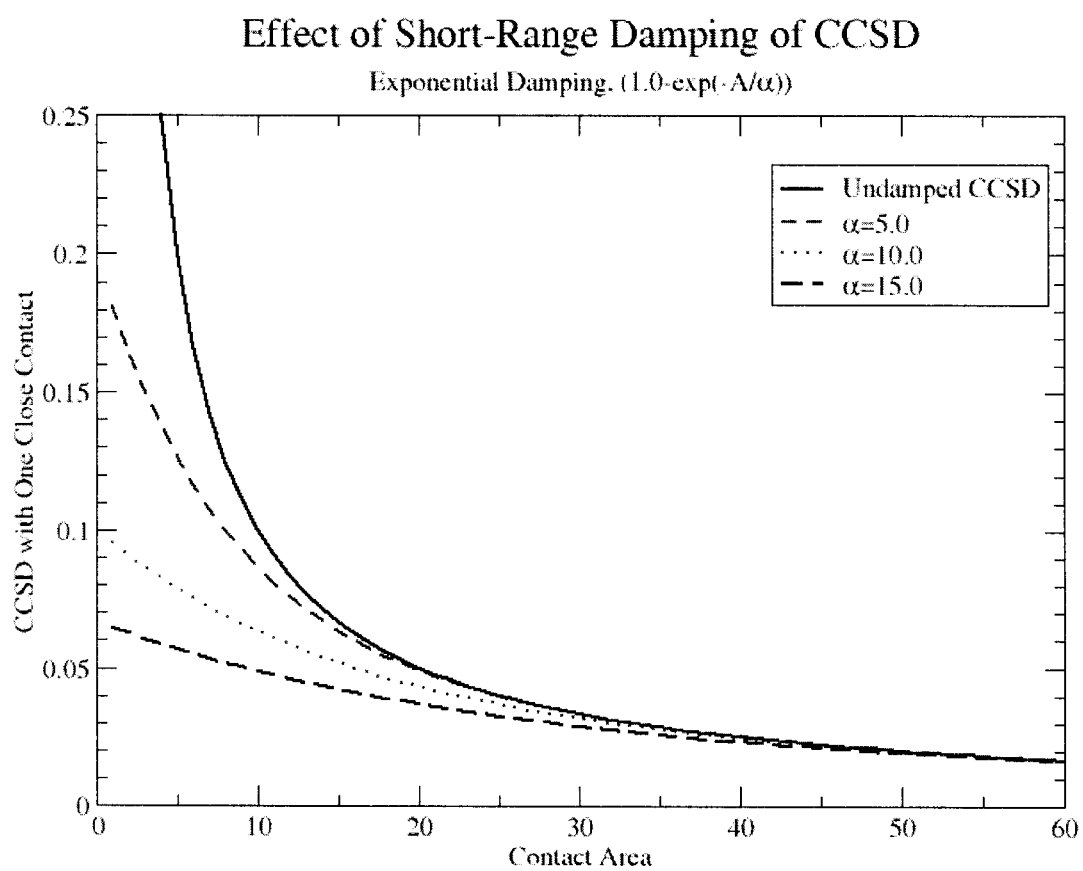
FIG. 7 shows exponential damping of 1/S, where S is contact area.

In some embodiments, the method comprises damping a CCSD. In certain limits, such as $SA_{Ng} \rightarrow 0$ or $SA_{rec} \rightarrow 0$, a singularity in CCSD occurs. The latter limit is the more relevant one since that contact can get very small, while the contact with other ligand residues rarely approach that limit. A standard method to damp a polynomial singularity is exponential damping:

$$\frac{1}{S}(1 - e^{-\beta S}) \sim \frac{1}{S}(\beta S + O(S^2)) \rightarrow \beta + O(S), S \rightarrow 0$$

where β is a numerical damping parameter, which has to be parameterized. Smaller β. results in greater damping. It is common to reformulate the damping parameter as $$\alpha = \frac{1}{\beta}$$

so that a larger value means a greater damping. The effect of damping is illustrated in FIG. 7. Values of the damping parameter α can be greater than 0, and in preferred embodiments has an upper limit of about 10, 20, 30, 40 and 50. Exemplary values of α are about 20 to about 25.

In some embodiments, the method is performed on a complex and then one of the members of the complex is altered to result in a second complex comprising a conformationally altered binding partner. The method is then repeated on one of the binding partners. In some of these embodiments, altering the sequence or conformation of one binding partner may result in a change in the conformation of the other binding partner. Thus, in some embodiments, a method further comprises changing the conformation of a first or second protein to provide the first protein in a second conformation and repeating steps of the method on the first protein in the second conformation.

Operation

In exemplary embodiments, the methods herein are implemented mechanically using a computer or computers in a larger system within a computer-modeling suite of software. In some embodiments, a script calls an addon for input structures and possibly trajectory frames. The new addon will in turn use the solvent accessible surface area addon, "SAVolumeArea" to compute the various surface areas and the number of contacts to obtain close atoms, and distance measurements from data sources to evaluate the contact potential. The addon returns three Python dictionaries of Python dictionaries, one of which might look like this:

{'ligand': {A/21.ALA: 0.4, A/22.ILE: 0.5, . . . },
'receptor': {A/21.ALA: 0.2, A/22.ILE: 'N/A', . . . }}

The keys of the first level, ligand and receptor, inform whether the quantity is for contacts within the ligand or to the receptor, respectively. The keys of the second level are residue objects in the set. For the three dictionaries, the values that correspond to these residue keys are selected from the CCSDs, the contact surface area and the contact potential. In case the contact surface area is zero, the corresponding CCSD value is 'N/A'.

The method may also be practiced without any receptor, in which case the dictionary that is returned only has one key in the first level.

Implementation in a Computer System

The methods described may be implemented as computer programs that are executed on a computer system comprising a processor, a memory (or data storage system) and a clock. A computer program is a set of instructions that can be used, directly or indirectly, in a computer to perform a certain activity or to bring about a certain result. A computer program can be written in any form of programming language, including compiled or interpreted languages, and it can be deployed in any form, including as a stand-alone program or as a module, component, subroutine, function, procedure or other unit suitable for use in a computing environment. The methods thus are performed on a computer system programmed to perform the steps of the method.

The processor is used to control the operation of the computer system. The processor comprises one or more components. For a multi component processor, one or more components may be located remotely relative to the others, or configured as a single unit. Furthermore, a processor can be embodied in a form having more than one processing unit, such as a multi-processor configuration, and should be understood to collectively refer to such configurations as well as a single-processor-based arrangement. One or more components of the processor may be of an electronic variety defining digital circuitry, analog circuitry, or both. A processor can be of a programmable variety responsive to software instructions, a hardwired state machine, or a combination of these.

It will be appreciated by one of skill in the art that a processor comprising instructions for performing any method disclosed herein is physically distinct from a processor that does not comprise such instructions. In other words, any given processor must be physically transformed to comprise instructions for performing any method disclosed herein.

Among its many functions, the memory in conjunction with the processor is used to store data as a process is being effected. A memory can include one or more types of solid state memory, magnetic memory, or optical memory, just to name a few. By way of nonlimiting example, the memory can include solid state electronic random access memory (RAM), sequential access memory (SAM), such as first-in, first-out (FIFO) variety or last-in, first-out (LIFO) variety, programmable read only memory (PROM), electronically programmable read only memory (EPROM), or electronically erasable programmable read only memory (BEPROM); an optical disc memory (such as a DVD or CD-ROM); a magnetically encoded hard disc, floppy disc, tape, or cartridge media; or a combination of these memory types. In addition, the memory may be volatile, non-volatile, or a hybrid combination of volatile, non-volatile varieties. The memory may further include removable memory which can be in the form of a non-volatile electronic memory unit, optical memory disk (such as a DVD or CD-ROM); a magnetically encoded hard disk, floppy disk, tape, or cartridge media; or a combination of these or other removable memory types.

The processor and memory can be supplemented by or incorporated in application-specific integrated circuits (ASICs). When read into the processor of the computer, which is thus physically transformed, and executed or further processed before execution, the instructions of the program cause the programmable computer to carry out the various operations described herein. The processor and the memory are typically connected by a bus.

The clock is used to time events in the system. As should be appreciated, the clock can be incorporated into the processor or can be a stand-alone component. Further, the clock can be hardware and/or software based.

To provide for interaction with a user, the invention can be implemented on a computer system comprising a display device such as, for example, a cathode ray tube (CRT) or liquid crystal display (LCD) monitor for displaying information to the user. The user can provide input, for example, via a keyboard, a touch screen or a pointing device such as a mouse or a trackpad.

The different aspects and embodiments described herein can be implemented in a computer system that includes a backend component such as a data server, a middleware component such as an application server or an Internet server, or a front end component such as a client computer having a user interface, Internet browser or any combination thereof. The components of the system can be connected by any form or medium of digital data communication.

The present system and methods can be implemented on hardware in a variety of configurations. Thus, in some embodiments, computational processes are performed in parallel on nodes of a computer cluster, in a distributed computing system or on graphics processing units as these configurations are understood in the art.

In one aspect, the invention provides a computer system for performing any method described herein. In one embodiment, the computer system comprises a clock, a memory and a processor comprising instructions for performing any method described herein.

In one aspect, the invention provides a computer system for quantifying the quality of packing for a residue comprising one or more residue atoms in a first protein in a first conformation, wherein the computer system comprises (1) a clock, (2) a memory and (3) a processor comprising instructions for performing the method, wherein the method comprises: (a) calculating one or more close contact potentials based on a distance between the one or more residue atoms and one or more environment atoms, (b) calculating a contact area of the one or more residue atoms that is exposed to the one or more environment atoms and (c) calculating a close contact surface density (CCSD) by dividing the sum of the one or more close contact potentials by the contact area. In exemplary embodiments, the method further comprises damping the CCSD.

A computer program disclose herein can be stored on a computer-readable storage system. Examples of storage systems include, without limitation, optical disks such as CD, DVD and Blu-ray Discs (BD); magneto-optical disks; magnetic media such as magnetic tape and internal hard disks and removable disks; semi-conductor memory devices such as EPROM, EEPROM and flash memory; RAM; and other types of memory.

A computer-readable storage system may be physically transformed such that it contains a computer program. It will be appreciated by one of skill in the art that a computer-readable storage system comprising instructions for performing any method disclosed herein is physically distinct from a computer-readable storage system that does not comprise such instructions. In other words, any given computer-readable storage system must be physically transformed to comprise instructions for performing any method disclosed herein. A computer-readable storage system comprising computer executable instructions, such as instructions for performing any method disclosed herein, is physically configured so as to cause a computer interacting with the storage system to perform a process or a method. One of skill in the art will appreciate that a computer-readable storage system comprising computer executable instructions for performing any method disclosed herein, when accessed and read by a general purpose computer, will transform the general purpose computer into a special purpose computer.

Thus, in one aspect, the invention provides a computer-readable storage system comprising computer executable instructions for performing any method described herein. In one embodiment, a computer-readable storage system comprises computer executable instructions for a method of quantifying the quality of packing for a residue comprising one or more residue atoms in a first protein in a first conformation, wherein the method is performed on a computer programmed to perform the steps of the method, the method comprising: (a) calculating one or more close contact potentials based on a distance between the one or more residue atoms and one or more environment atoms, (b) calculating a contact area of the one or more residue atoms that is exposed to the one or more environment atoms and (c) calculating a close contact surface density (CCSD) by dividing the sum of the one or more close contact potentials by the contact area. In exemplary embodiments, the method further comprises damping the CCSD.

Applications

The methods and systems described herein have a number of useful biological applications. In particular, the methods and systems may be used to engineer any number of molecules with improved characteristics, such as improved stability, packing or binding affinity to binding partners.

In one aspect, the invention provides a method of engineering a variant protein relative to a parent protein, the method comprising (a) performing a computer implemented method described herein on the parent protein to provide a first CCSD; (b) mutating one or more residues of the parent protein to provide the variant protein, (c) performing the computer implemented method selected in the previous performing step (a) on the variant protein to provide a second CCSD and (d) making the variant protein if the second CCSD compared to the first CCSD indicates comparable or improved stability of the variant protein relative to the parent protein.

A "protein" is any polypeptide, typically having a definite three-dimensional structure under physiological conditions. A "variant" protein is a protein that contains one or more mutations (e.g., insertions, deletions and substitutions) in its sequence relative to a reference "parent" protein. In exemplary embodiments, a variant protein is characterized by substituting 1%, 2%, 3%, 4%, 5%, 6%, 7%, 8%, 9%, 10%, 11%, 12%, 13%, 14%, 15%, 16%, 17%, 18%, 19% or 20% of the amino acids (or residues) of a parent protein. In some embodiments, the parent protein is a wild-type protein.

In one aspect, the invention provides a method of engineering a variant protein complex relative to a parent protein complex, the method comprising (a) performing a computer implemented described herein on the parent protein complex to provide a first CCSD; (b) mutating one or more residues of the parent protein complex to provide the variant protein complex, (c) performing the computer implemented method selected in the previous performing step on the variant protein complex to provide a second CCSD and (d) making the variant protein complex if the second CCSD compared to the first CCSD indicates comparable or improved stability of the variant protein complex relative to the parent protein complex.

In one aspect, the invention provides a method of making a ligand that selectively binds to a protein, the method comprising (a) performing the computer implemented method of any of claims 1-10 on a first complex comprising the protein bound to a first ligand to provide a first CCSD; (b) performing the computer implemented method selected in the previous performing step (a) on a second complex comprising the protein bound to a second ligand to provide a second CCSD, (c) making the second ligand if the second CCSD compared to the first CCSD indicates comparable or improved stability of the second complex relative to the first complex.

In one aspect, the invention provides a computer implemented method of constructing a protein homology model, the method comprising (a) performing a computer implemented method described herein on a protein or protein complex in a first conformation to provide a first CCSD; (b) performing a deterministic or stochastic simulation of the protein or protein complex to provide the protein or protein complex in a second conformation; (c) performing the computer implemented method selected in the previous performing step (a) on the protein or protein complex in the second conformation to provide a second CCSD; and (d) accepting the protein or protein complex in the second conformation if the CCSD has improved for one or more residues of the protein or protein complex. In exemplary embodiments, the method of constructing a protein homology model is performed on a computer system comprising (1) a clock, (2) a memory, and (3) a processor and wherein each step of the method is performed utilizing the processor.

In some embodiments, the step of performing a deterministic or stochastic simulation comprises performing a molecular dynamics simulation. Simulation models that contain no random variables are classified as deterministic. Deterministic models have a known set of inputs which will result in an unique set of outputs. In biological applications, deterministic simulations, such as molecular dynamics simulations are typically based on ordinary differential equations. These simulations are well known in the art and are reviewed in Adcock and McCammon, Chem Rev, 2006, 106:1589-615.

A stochastic simulation utilize one or more random variables as inputs. A number of stochastic methods are known in the art, and include, for example, Monte Carlo and Metropolis Monte Carlo methods. Monte Carlo methods form a class of computational algorithms that rely on repeated random sampling to compute their results. These methods vary, but typically include the steps of: (1) defining a domain of possible inputs; (2) generating inputs randomly from a probability distribution over the domain; (3) performing a deterministic computation on the inputs; and (4) aggregating the results. See, for example, Sobol, I. M. A Primer for the Monte Carlo Method. Boca Raton, Fla.: CRC Press, 1994. The Metropolis criterion in a Monte Carlo simulation introduces a temperature dependent energy function conditional that follows detailed balance to achieve equilibrium sampling of states. See Metropolis et al., The Journal of Chemical Physics, 1953, 21: 1087-1092.

Thus, in some embodiments, the step of performing a deterministic or stochastic simulation comprises performing a Monte Carlo simulation.

In some embodiments, the method comprises performing a Monte Carlo sampling of the protein backbone degrees of freedom for a plurality of backbone atoms and a Monte Carlo sampling of discretized side-chain degrees of freedom for a plurality of side-chain atoms.

The invention also provides proteins, protein complexes, ligands and other molecules that are made according to the methods disclosed herein.

EXAMPLES

In testing and validation of the close contact surface density (CCSD) method, the quality of packing of areas of residues that face a binding partner, and in some cases with other residues in the amino acid chain, have been quantified. The method can be used on a single structure or on a trajectory. In the examples, the values of the relevant parameters were: $r_c=3.6$ Å and $d=0.2$ Å. Contact areas were computed as described above.

The deployed Dockground 3.0™ benchmark database of high-resolution protein complex structures is used to obtain statistics on the distribution of the CCSD per residue type at protein-protein interfaces. The Dockground™ project is designed to provide resources for the development of such techniques as well as increase our knowledge of protein interfaces. For background on Dockground™, see Douguet D et al., "DOCKGROUND resource for studying protein-protein interfaces", Bioinformatics, 2006 November; 22(21): 2612-2618; Gao Y et al., "DOCKGROUND system of databases for protein recognition studies: Unbound structures for docking", Proteins, 2007 Sep. 5; 69(4): 845-851; and Liu S et al., "Dockground protein-protein docking decoy set", Bioinformatics, 2008; 24(22): 2634-2635.

The same structures were used to obtain data on the ligand-only packing.

Example 1

Residue Type Distributions

Figure 2:
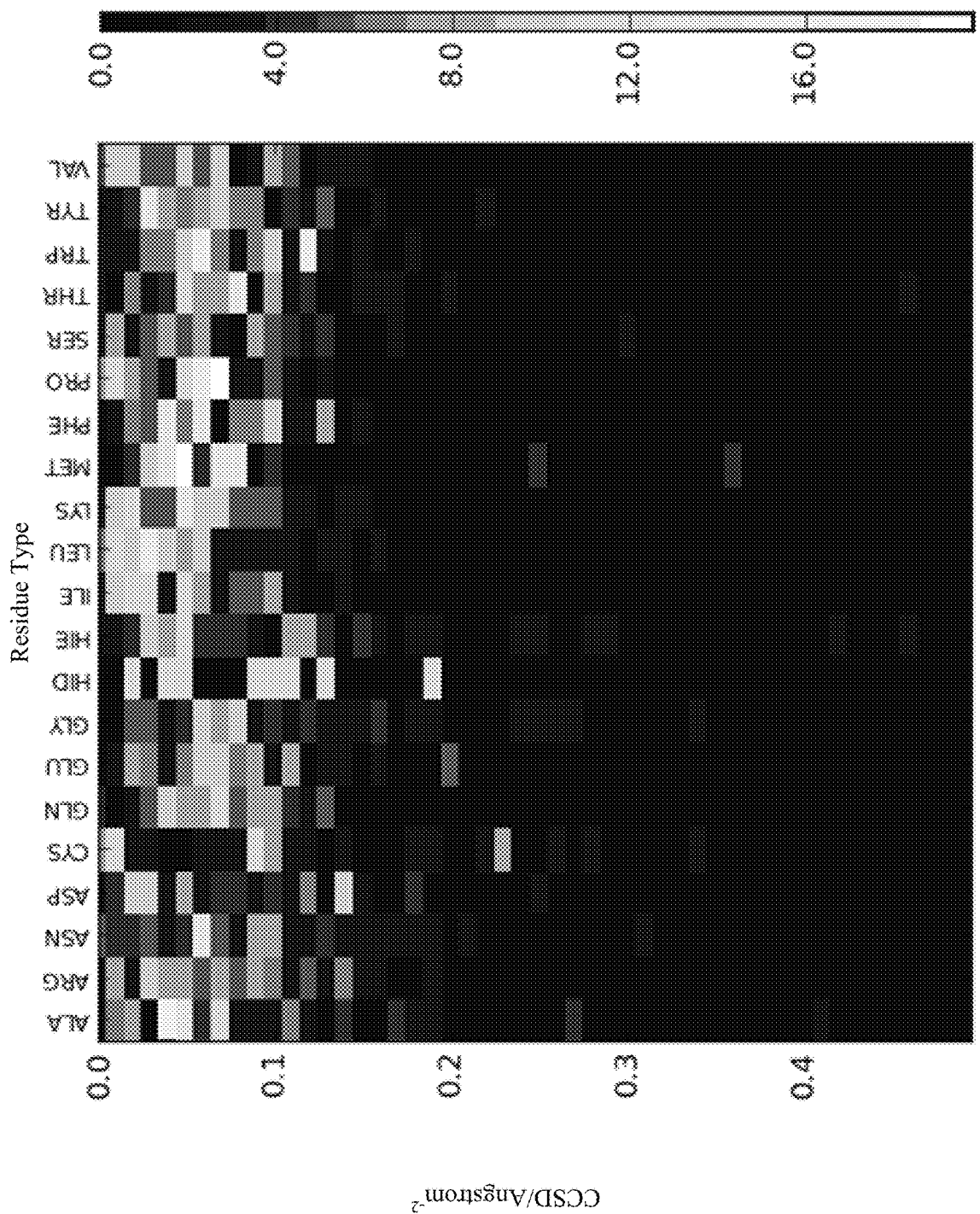
FIG. 2 shows a normalized histogram of the CCSDs calculated for all residues types at the receptor-ligand interface in the Dockground 3.0™ benchmark complexes. All residue types have similar magnitudes, almost all of which are in the range 0.0 to 0.2 Å$^{-2}$. The y-axis is CCSD/Angstrom$^{-2}$, the x-axis is residue type and the scale on the right is population.

The CCSD was computed for all interface residues of the ligands in the Dockground 3.0™ dataset and decomposed into per-residue type data. The normalized histograms are illustrated in FIG. 2. A colour towards the white end of the spectrum means a large population, while a colour towards the dark end means a small population.

In Table 1, statistics from the CCSD distributions are shown for the subset of data points where the CCSD value is strictly greater than zero and strictly smaller than 0.25 Å$^{-2}$.

TABLE 1

Statistics for residues in the ligands with non-zero surface area to receptor in the benchmark complexes, only including values in the range (0.0, 0.25 Å$^{-2}$)

| Residue Type | N @ interface | Average CCSD | Std. Dev. (σ) |
|---|---|---|---|
| ALA | 102 | 0.075 | 0.048 |
| ARG | 140 | 0.086 | 0.052 |
| ASN | 133 | 0.095 | 0.058 |
| ASP | 123 | 0.092 | 0.059 |
| CYS | 50 | 0.099 | 0.073 |
| GLN | 109 | 0.085 | 0.05 |
| GLU | 150 | 0.09 | 0.054 |
| GLY | 154 | 0.099 | 0.058 |
| HID | 12 | 0.096 | 0.049 |
| HIE | 62 | 0.088 | 0.056 |
| ILE | 87 | 0.066 | 0.045 |
| LEU | 137 | 0.057 | 0.042 |
| LYS | 173 | 0.068 | 0.048 |
| MET | 46 | 0.06 | 0.021 |
| PHE | 93 | 0.081 | 0.044 |
| PRO | 91 | 0.057 | 0.032 |
| SER | 206 | 0.087 | 0.058 |
| THR | 154 | 0.085 | 0.048 |
| TRP | 47 | 0.083 | 0.041 |
| TYR | 141 | 0.082 | 0.055 |
| VAL | 109 | 0.07 | 0.047 |

The numbers are of comparable magnitude for different residues, thereby demonstrating one of the advantages of the methods of the invention: a quantification of the packing quality that is comparable between different types of residues.

A few residues, such as LEU, ILE, MET and PRO, have somewhat lower averages than the rest. The three first are hydrophobic residues and are known to occupy the core of the interface. Also, they have aliphatic side-chains, which set them apart from PHE, TYR and TRP, which are three residue types also known to occupy the core of the interface, but that provided typical CCSD averages.

The lower value of the CCSD for LEU, ILE and MET at protein interfaces may be an indicator that these side-chains are on average more difficult to pack very well compared to aromatic side-chains. Finally, PRO is not common at the interface, and usually occupies special positions in the fold, often being an exceptional residue in many cases.

Figure 3:
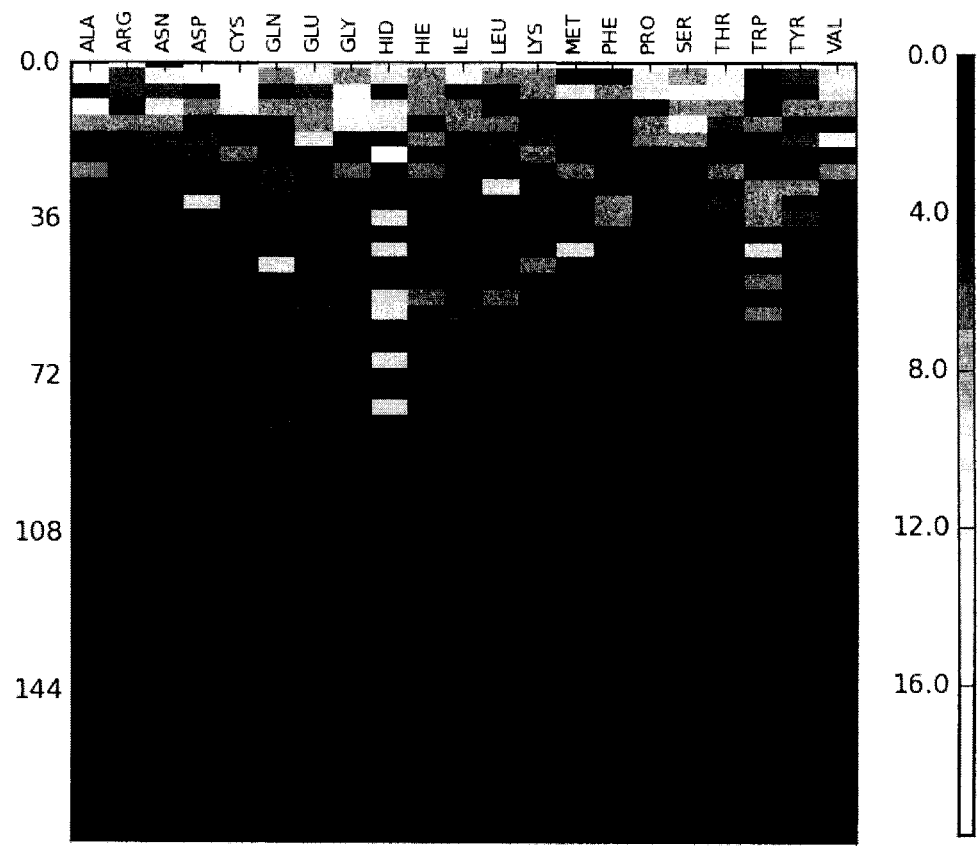
FIG. 3 shows a normalized histogram of the receptor contact area for all residue types in the ligands in the benchmark complexes. The y-axis is contact area/Angstrom$^2$, the x-axis is residue type and the scale on the right is population.

In FIG. 3, the distributions of contact areas are shown for reference. The CCSD values are obtained by computing the packing of the ligand residues by the other ligand residues.

In Table 2, the statistics for each residue type are shown for a scenario in which only contacts including 1-5 or beyond are counted. In Table 3 the same statistics are shown if only contacts including 1-3 or beyond are counted.

TABLE 2

Statistics for residues in the ligands being packed by other ligand residues only; only contacts including 1-5 or beyond are counted

| Residue Type | N | Average | Std. Dev. |
|---|---|---|---|
| ALA | 1735 | 0.069 | 0.023 |
| ARG | 1153 | 0.076 | 0.023 |
| ASN | 1170 | 0.086 | 0.024 |
| ASP | 1415 | 0.086 | 0.026 |
| CYS | 517 | 0.059 | 0.02 |
| GLN | 1065 | 0.079 | 0.024 |
| GLU | 1618 | 0.078 | 0.026 |
| GLY | 1791 | 0.065 | 0.023 |
| HID | 92 | 0.086 | 0.024 |
| HIE | 506 | 0.081 | 0.023 |
| ILE | 1239 | 0.061 | 0.019 |
| LEU | 2310 | 0.058 | 0.019 |
| LYS | 1540 | 0.07 | 0.022 |
| MET | 465 | 0.064 | 0.021 |
| PHE | 1045 | 0.067 | 0.02 |
| PRO | 1241 | 0.066 | 0.021 |
| SER | 2098 | 0.077 | 0.025 |
| THR | 1624 | 0.076 | 0.023 |
| TRP | 454 | 0.07 | 0.02 |
| TYR | 946 | 0.074 | 0.021 |
| VAL | 1840 | 0.061 | 0.018 |

TABLE 3

Statistics for residues in the ligands being packed by other ligand residues only; only contacts including 1-3 or beyond are counted

| Residue Type | N | Average | Std. Dev. |
|---|---|---|---|
| ALA | 1735 | 0.152 | 0.026 |
| ARG | 1153 | 0.141 | 0.026 |
| ASN | 1170 | 0.165 | 0.026 |
| ASP | 1415 | 0.167 | 0.025 |
| CYS | 517 | 0.138 | 0.021 |
| GLN | 1065 | 0.152 | 0.027 |
| GLU | 1618 | 0.158 | 0.027 |
| GLY | 1791 | 0.15 | 0.022 |
| HID | 92 | 0.148 | 0.026 |
| HIE | 506 | 0.148 | 0.025 |
| ILE | 1239 | 0.122 | 0.022 |
| LEU | 2310 | 0.119 | 0.023 |
| LYS | 1540 | 0.146 | 0.027 |
| MET | 465 | 0.125 | 0.025 |
| PHE | 1045 | 0.121 | 0.023 |
| PRO | 1241 | 0.168 | 0.031 |
| SER | 2098 | 0.165 | 0.027 |
| THR | 1624 | 0.156 | 0.026 |
| TRP | 454 | 0.12 | 0.023 |
| TYR | 946 | 0.129 | 0.022 |
| VAL | 1840 | 0.128 | 0.022 |

The trends are very similar between the two ways of treating the bonded contacts, although numerically, they differ significantly.

A comparison between Tables 1 and 2 shows that in the case where only contacts including 1-5 and beyond are counted within the ligand (Table 2), the magnitude of the CCSD is very similar to the magnitude of the CCSD where only non-bonded contacts with the receptor are accounted for (Table 1). This observation is congruent with the fact that many biomolecular force-fields do not compute non-bonded interactions between 1-2, 1-3 contacts and significantly scale the 1-4 non-bonded interaction.

Example 2

Improving and Worsening Packing

The Rac/p67phox protein-protein complex (PDB Accession Record 1E96, also part of the DockGround 3.0™ dataset) was used to further illustrate the capabilities of CCSD by studying residue swaps in a few selected positions followed by a structural analysis where the packing quality was assessed through 3D graphical rendering of the structures. The positions ASN26 and GLU31 in chain A, designated A/26.ASN and A/31.GLU, which contact the other protein, chain B, were found to have a high CCSD. The position A/27.ALA, also at the interface, was found to have a low CCSD. A number of swaps were made and the surrounding residues were repacked. The CCSD for the residue in the swapped position was computed and the results are shown in Table 4.

TABLE 4

Specific swaps that have been visually inspected to verify that the CCSD is informative; structure is 1E96 and CCSD is in units of Å$^{-2}$

| Position | Residue | CCSD | Comment |
|---|---|---|---|
| A/26 | ASN* | 0.141 | ASN side-chain got pi-pi like stacking with B/104.ASN, forms a lot of contacts. |
| A/26 | GLN | 0.087 | Amide group cannot contact B/104.ASN, but points away from chain B. |
| A/26 | LEU | 0.142 | Heavy atoms in LEU side-chain lie almost exactly like heavy atoms in ASN. |
| A/26 | LYS | 0.119 | Loses contacts with chain B; instead forms contacts with ligand, so area to chain B reduced. |
| A/26 | PHE | 0.138 | Forces reorientation of B/104.ASN to regain pi-pi stacking. |
| A/26 | THR | 0.100 | Loses some contacts, but also gains some. |
| A/27 | ALA* | 0.045 | ALA faces chain B completely, but points into a void; poorly packed. |
| A/27 | GLN | 0.106 | GLN is of perfect size to fill up the cavity and makes many new contacts with chain B. |
| A/27 | LEU | 0.043 | LEU is smaller than GLN and cannot fill up the cavity; as bad as ALA. |
| A/27 | LYS | 0.106 | LYS fills up cavity, and the NH3 group can be put out of cavity without clash. |
| A/27 | PHE | 0.079 | Part of void is filled. |
| A/27 | VAL | 0.046 | Too small to fill void, just as bad as ALA. |
| A/31 | GLU* | 0.150 | GLU carboxyl group makes many good polar contacts. |
| A/31 | ARG | 0.050 | Cannot occupy delta-carbon position of GLU, polar head group thrown out into solvent. |
| A/31 | ASP | 0.137 | Loses GLU contacts, but gains some new by assuming a different orientation. |
| A/31 | LEU | 0.030 | Does not fill delta-carbon position of GLU and one of its delta-carbon got no contacts. |
| A/31 | PHE | 0.053 | Does not fill void. |

*Wild-type.

It was confirmed that all cases make structural sense and polar and non-polar contacts that are either lost or gained following the mutations are reasonably quantified by the CCSD method. In neither case was a clash the cause of the large value.

Example 3

Trajectory Analysis: Insulin Receptor "IR_11"

In a molecular dynamics trajectory analysis of the simulation of the IR_11 protein-protein complex from the Insulin Receptor (PDB Accession Record 2DTG), a partial breaking apart of the complex is known to occur. The Amber99 force field was used for the protein, and TIP3P was used for water. The simulation was run in the NPT ensemble with a 2.0 fs time-step with periodic boundary conditions and a 12 Å non-bonded cut-off.

To make the analysis less time-consuming, only every 30th frame was sampled leading to a total of 659 frames.

Figure 4:
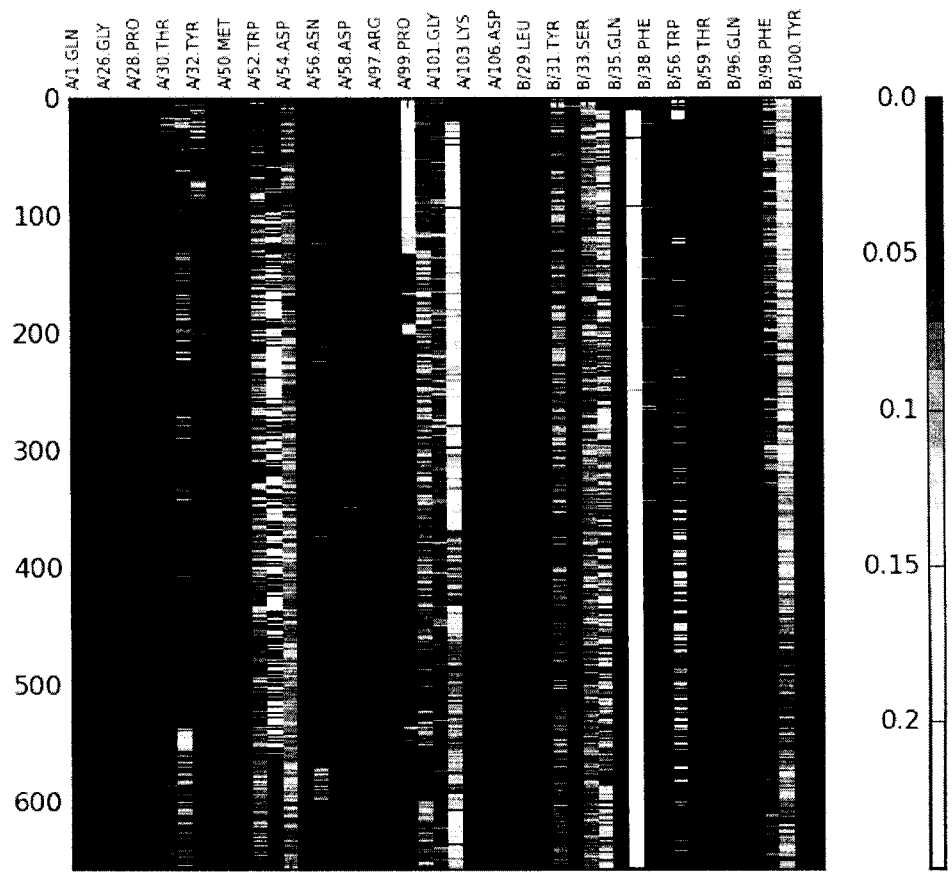
FIG. 4 shows a graph of CCSD for interface residues in the insulin receptor complex (IR_11) as a function of frame number in a molecular dynamics trajectory. Any value higher than 0.25 Å$^{-2}$ is reported as 0.25. The y-axis is trajectory frame, the x-axis is residue and the scale on the right is CCSD/Angstrom$^{-2}$.

In FIG. 4, the CCSD is plotted as a function of trajectory frame for interface residues. The maximum value is set to 0.25 Å$^{-2}$.

Figure 5:
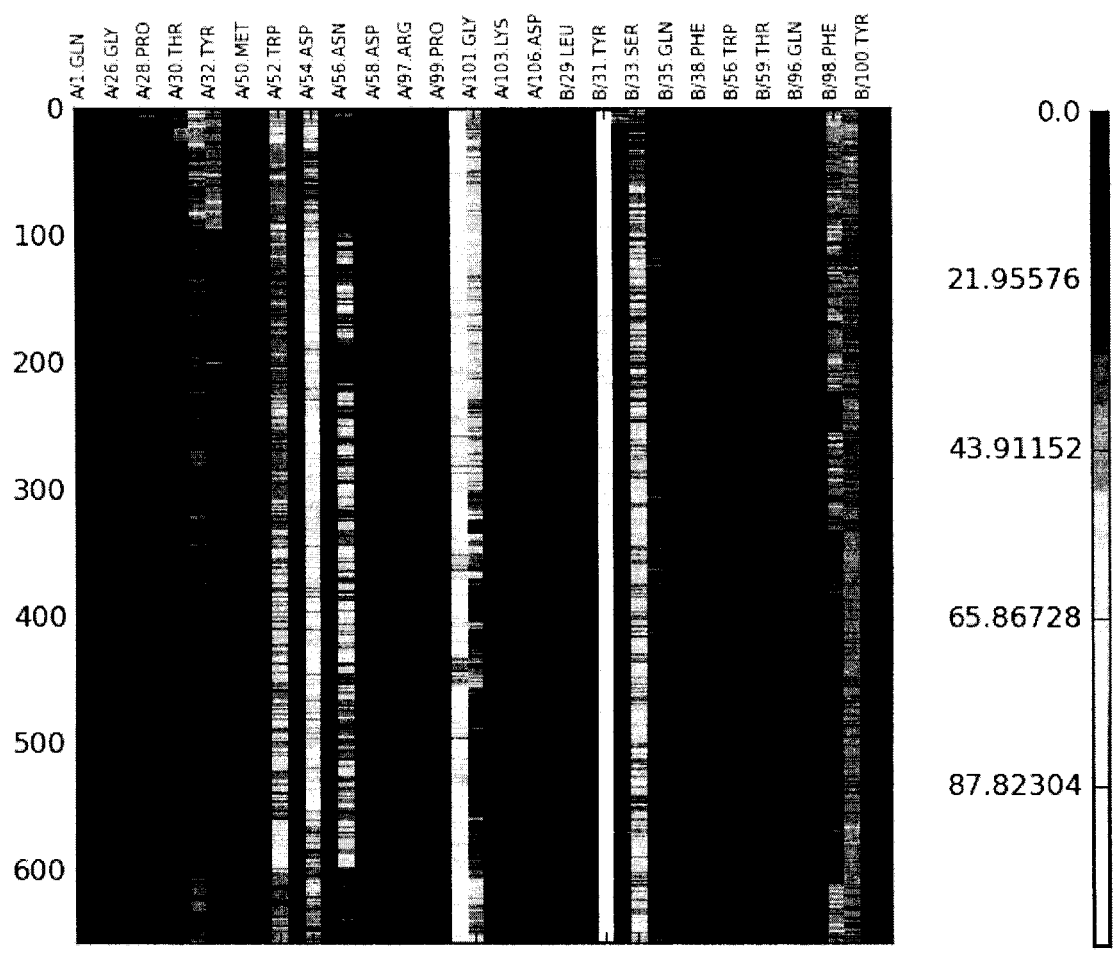
FIG. 5 shows a graph of the receptor contact area for ligand residues at the interface of the insulin receptor complex as a function of frame number in a molecular dynamics trajectory. The y-axis is trajectory frame, the x-axis is residue and the scale on the right is contact area/Angstrom$^2$.

CCSD values for B/36.LYS are shown in FIG. 4 along the unlabeled trajectory frame axis that is between the trajectory frame axes of B/35.GLN and B/38.PHE. Data for B/36.LYS show a consistently high value. A closer inspection of the structure and the contact area to the receptor, (see FIG. 5), shows that B/36.LYS has only a salt-bridge contact with the receptor. The result is correct therefore in the sense that the little contact B/36.LYS got with the receptor is a very well-packed contact.

CCSD values for A/53.GLY are shown in FIG. 4 along the unlabeled trajectory frame axis that is between the trajectory frame axes of A/52.TRP and A/54.ASP. A/53.GLY shows a great deal of fluctuation, going from zero to very high. This is an indication of that A/53.GLY is fluctuating between having a close contact and not having any contact at all. This is reasonable behavior given the small size of glycine.

An interesting side-effect of this analysis is that the breaking apart of the complex becomes very evident. The contacts in the first band from left disappears or are weakened after a few frames in the trajectory.

Figure 6:
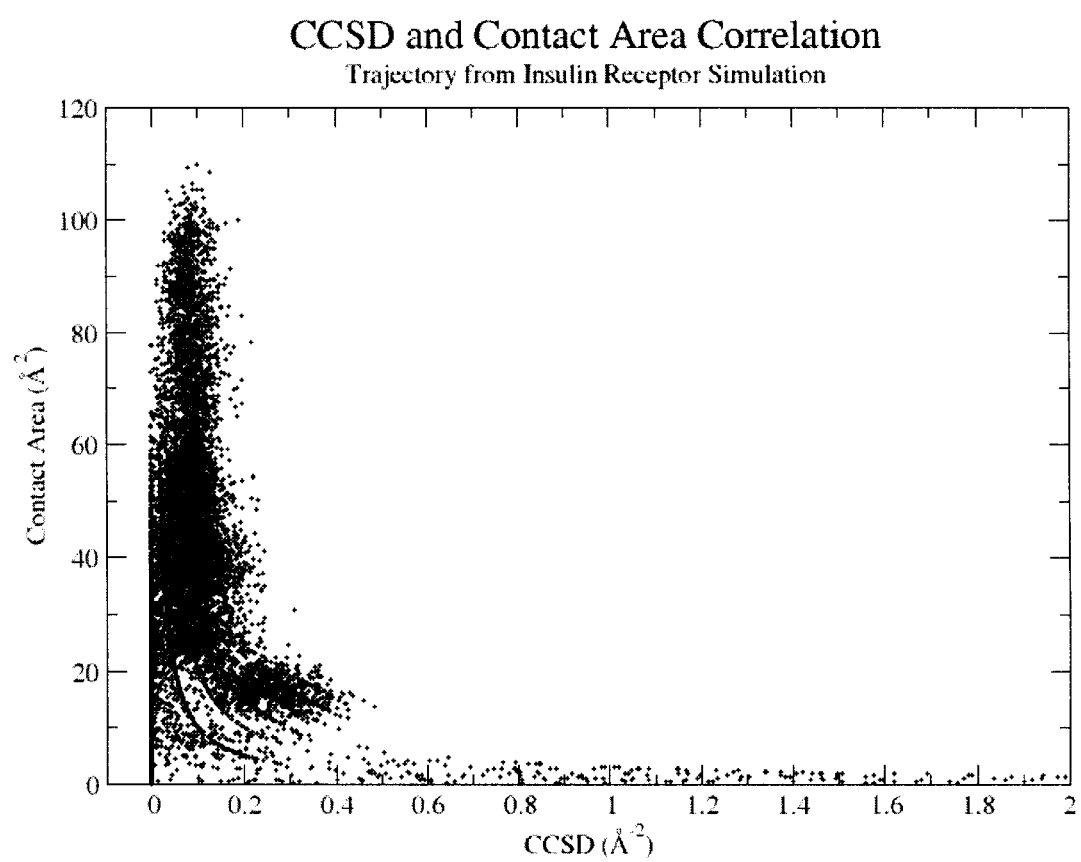
FIG. 6 shows a graphical representation of the correlation between contact area and CCSD for all ligand residue types at the interface of the insulin receptor complex for all frames in a molecular dynamics trajectory.

In FIG. 6, the correlation between contact area and CCSD is shown for all residue types at the interface to the receptor for all frames in the trajectory.

This illustrates that exceptionally high CCSDs are a result of numerical instabilities. Thus, a CCSD obtained from a contact area less than about 10 to 15 Å$^2$, or a CCSD greater than about 0.25 to 0.30 Å$^2$ may, in some cases, be less informative of the packing quality. To mitigate the effects of numerical instabilities, it may be advantageous to damp the CCSD, particularly when the contact area is small.

These data also provide information on the stability of CCSD to minor structural fluctuations. In most cases, unless the contact area is very small and the CCSD is not damped, the CCSDs are qualitatively stable.

The methods thus have been shown to be useful for quantifying the quality of the packing consistent with visual inspection of the structure, and thus make it possible to identify mutations that improve or worsen contacts.

Example 4

The quality of packing is related to the ubiquitous dispersion interaction or the London forces. A more tightly packed structure involves a stronger interaction, and hence is expected to generally imply a greater binding affinity between two proteins, or improved thermodynamic stability of the folded state vis-à-vis the unfolded state. The CCSD metric has been shown to indeed correlate with experimental affinity data.

A set of protein complexes has been extensively studied experimentally by selectively mutating residues and measuring the change of the binding affinity. The complexes are: human growth hormone in complex with the receptor extracellular domain (PDB Accession Record 1A22), ribonuclease inhibitor with angiogenin complex (PDB Accession Record 1A4Y), barnase-barstar complex (PDB Accession Record 1BRS), *Escherichia coli* colicin E9 dnase domain in complex with immunity protein 1M9 (PDB Accession Record 1BXI), Bovine chymotrypsin complexed to BPTI (PDB Accession Record 1CBW), Alpha-Chymotrypsin with inhibitor turkey ovomucoid third domain (PDB Accession Record 1CHO), Idiotopic antibody D1.3 with antiidiotopic antibody E5.2 (PDB Accession Record 1DVF), Antibody-antigen complex A6 fab-IFNgammaR1-108 (PDB Accession Record 1JRH), TEM-1 beta-Lactamase with beta-Lactamase inhibitor protein (PDB Accession Record 1JTG), antigen-antibody complex, anti-hen egg white lysozyme antibody D1.3 with hen egg white lysozyme (PDB Accession Record 1VFB), antibody-antigen complex, anti-lysozyme HyHEL-10 with hen egg white lysozyme (PDB Accession Record 3HFM). The experimental observables, $\Delta\Delta G$ values, are thus obtained. The affinity data are available in separate publications, but have been compiled by Handel and co-workers. Chowdry, A. B.; Reynolds, K. A.; Hanes, M. S.; Voorhies, M.; Pokala, N.; Handel, T. M. *J. Comput. Chem.*, 2007, 28: 2378. In total, experimental data for 541 mutations were considered.

Using a high-quality in silico protein repacking technology, structural changes upon mutation were predicted for all 541 mutations. The CCSD was computed for each structure, and the change in CCSD compared to the wild-type structure was correlated with the experimental affinity to test the hypothesis that CCSD is predictive of the thermodynamic observable $\Delta\Delta G$.

In Table 5, the rank correlation between $\Delta\Delta G$ and the change of the CCSD Z-score is shown, along with the P-values estimated for the correlation coefficients. A warm mutant is defined as having a MG less than −0.6kcal/mol, a cold mutant is defined as having a $\Delta\Delta G$ greater than 0.6 kcal/mol.

TABLE 5

Rank Correlation Metrics between the Change of CCSD Z-score Versus Experimental Change of Binding Affinity

| Mutant Type | Spearman R | P-value | Kendall Tau | P-value |
| --- | --- | --- | --- | --- |
| All | −0.226 | 0.000 | −0.157 | 0.000 |
| Warm | −0.375 | 0.034 | −0.257 | 0.039 |
| Cold | −0.204 | 0.000 | −0.134 | 0.000 |

The rank correlations are non-zero and the P-values are very small in Table 5. Consequently, the value of the CCSD Z-score is predictive of the experimental observable $\Delta\Delta G$.

To further establish that the CCSD Z-score is predictive of the thermodynamic observable, a confusion matrix (or contingency table) is shown in Table 6. The confusion matrix shows how well the CCSD Z-score is able to classify a given in silico mutation into the binary categories of "increasing binding affinity" and "decreasing binding affinity". We define a positive value of the CCSD Z-score as a prediction of an increase in binding affinity, and a negative value as a prediction of a decrease.

TABLE 6

Confusion Matrix for the CCSD Z-score vis-a-vis Experimental $\Delta\Delta G$ Values; Ratios Show for Given Mutations how They Distribute Between Prediction and Experimental Reality

| | Experimental increase | Experimental decrease | Predicted probabilities |
| --- | --- | --- | --- |
| Predicted increase | 0.085 | 0.297 | 0.382 |
| Predicted decrease | 0.069 | 0.549 | 0.618 |

TABLE 6-continued

Confusion Matrix for the CCSD Z-score vis-a-vis Experimental ΔΔG Values; Ratios Show for Given Mutations how They Distribute Between Prediction and Experimental Reality

|  | Experimental increase | Experimental decrease | Predicted probabilities |
|---|---|---|---|
| Experimental probabilities | 0.154 | 0.846 | 1.000 |

Table 6 shows that of all mutations in the set, 15.4% have been experimentally determined to improve the binding affinity; of these 0.085/0.154=55.2% are predicted by the CCSD Z-score to increase binding affinity. In other words, the statistical sensitivity of the method is for the particular data set 55.2%. The statistical specificity is found to be 0.549/0.846=64.9%, which is an indicator of how well the CCSD Z-score correctly predicts a mutation that decreases the binding affinity as such. The likelihood ratio, defined as the sensitivity divided by one minus the specificity is therefore 1.57.

These results show that 1. the CCSD Z-score correlates with the experimental affinity; hence, if a set of mutations are ranked according to this metric, a higher percentage of mutations with a negative/positive MG value will be found in the upper/lower percentile of the distribution compared to random guessing,
2. the CCSD Z-score predicts if a given mutation increases or decreases the binding affinity with a better than random statistical accuracy.

These results are strong evidence that the CCSD Z-score is related to a thermodynamic property, ΔΔG of binding upon mutation, relevant to protein engineering and therefore can improve the accuracy and reduce the cost of structure guided, rational, computational protein engineering.

Examples 5, 6 and 7 present an analysis of the variation in the ccsd_receptor value with specific focus on the damping factor. The following models were used for analysis; for all models the damping parameter alpha-damping was varied from 0-30:

1. "Repeat 1-5": Four homology models of the Fc:FcR (IIIaF) complex created from an extensive iterative random walk sampling of side-chain and backbone conformations of the CH3 domains of the Fc:FcR complex; the only difference of the four models is the random seed used for the pseudo-random number generator that is used in the random walk sampling. The four models are labeled "repeat_1", "repeat_2", "repeat_3" and "repeat_5".
2. "Repeat_c1-5": Five homology models of the Fc:FcR (IIIaF) complex created using the same procedure as for Model one, with the only difference that the sampling is done for side-chains and backbone in the entire Fc. The five models are labeled "repeat_c1", "repeat_c2", "repeat_c3", "repeat_c4" and "repeat_c5".
3. Backrub trajectories: Two ensembles of structures obtained from
   (a) About one hundred snapshots from the random walk used to produce the model of repeat_1 above; and
   (b) Five snapshots obtained from a short backbone conformational sampling using a random-walk local to the residue positions in the vicinity of positions A/366, A/392, A/394, B/351, B/368, B/397, B/405 and B/407 in the CH3 domain of the Fc:FcR.

Details on the method used to efficiently sample backbone conformations of one or several backbone segments in a protein can be found in Betancour, J. Chem. Phys., 2005, 123: 174905.

Example 5

Analysis of CCSD_receptor Variation With Damping on Individual IR Models

Figure 8:
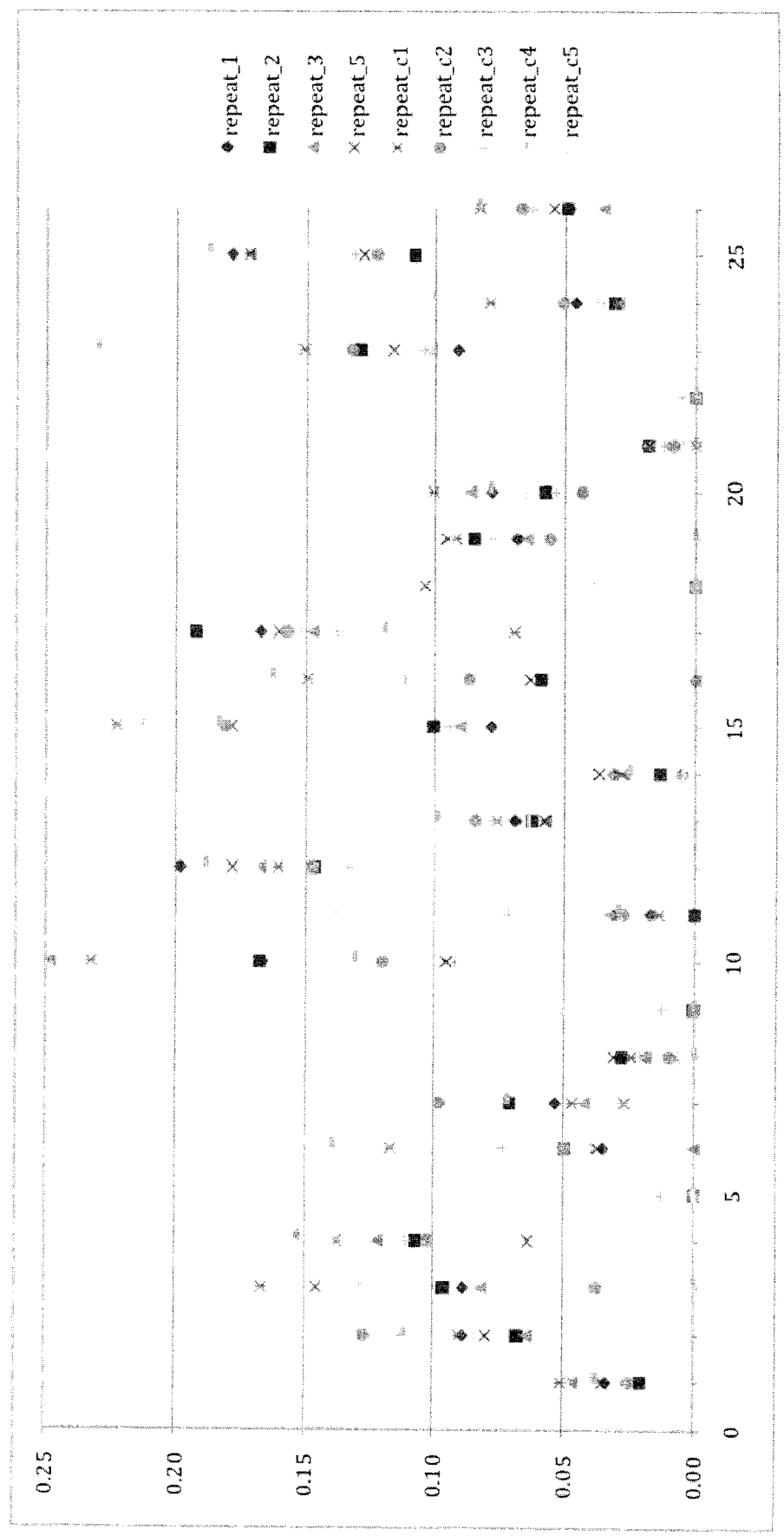
FIG. 8 shows CCSD_receptor values calculated using a close-cutoff of 3.6 Å and a damping factor with a damping parameter value of 0, according to Example 5. The y-axis is CCSD_receptor and the x-axis is the residue index as described in Table 7.
Figure 9:
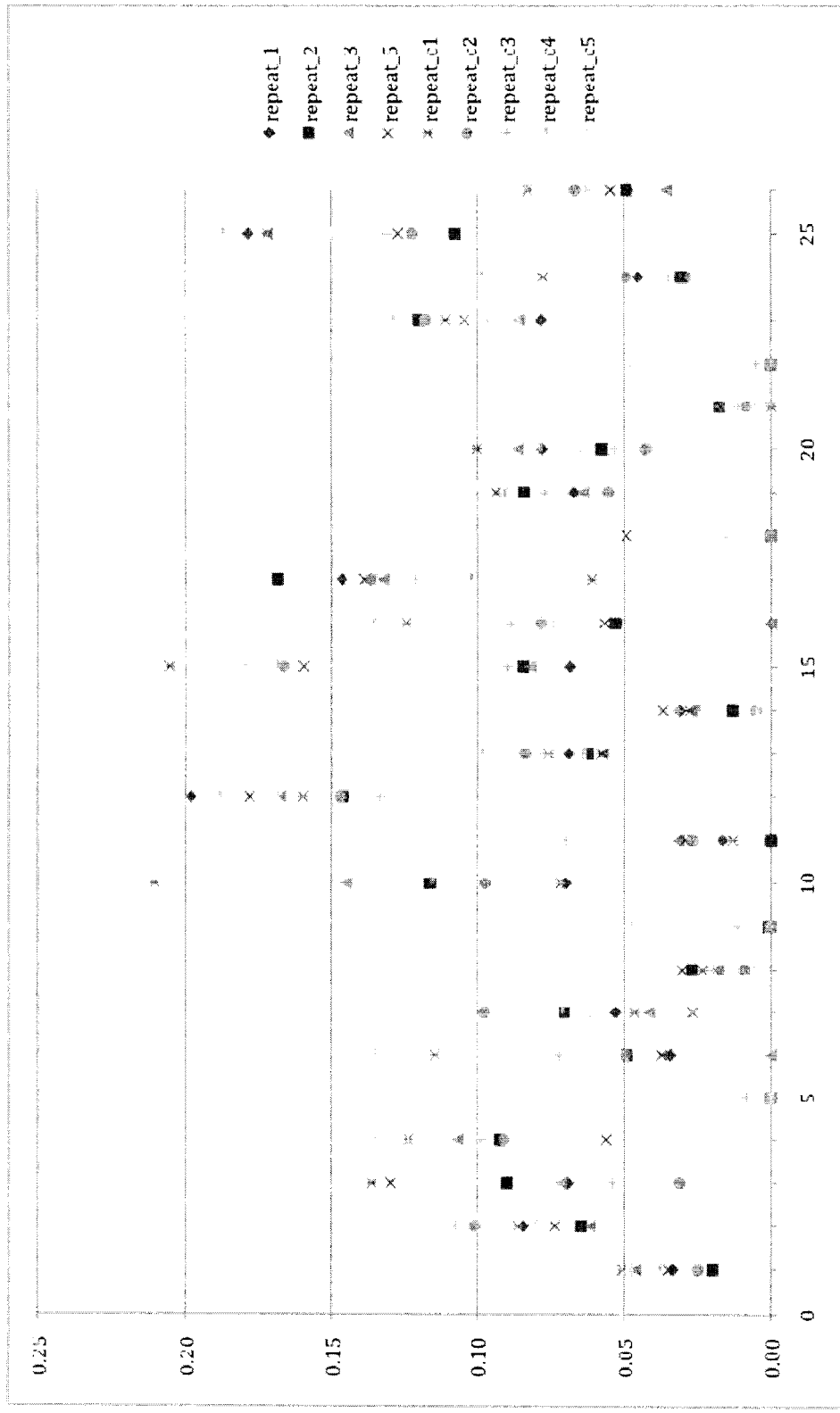
FIG. 9 shows CCSD_receptor values calculated using a close-cutoff of 3.6 Å and a damping factor with a damping parameter value of 15, according to Example 5. The y-axis is CCSD_receptor and the x-axis is the residue index as described in Table 7.
Figure 10:
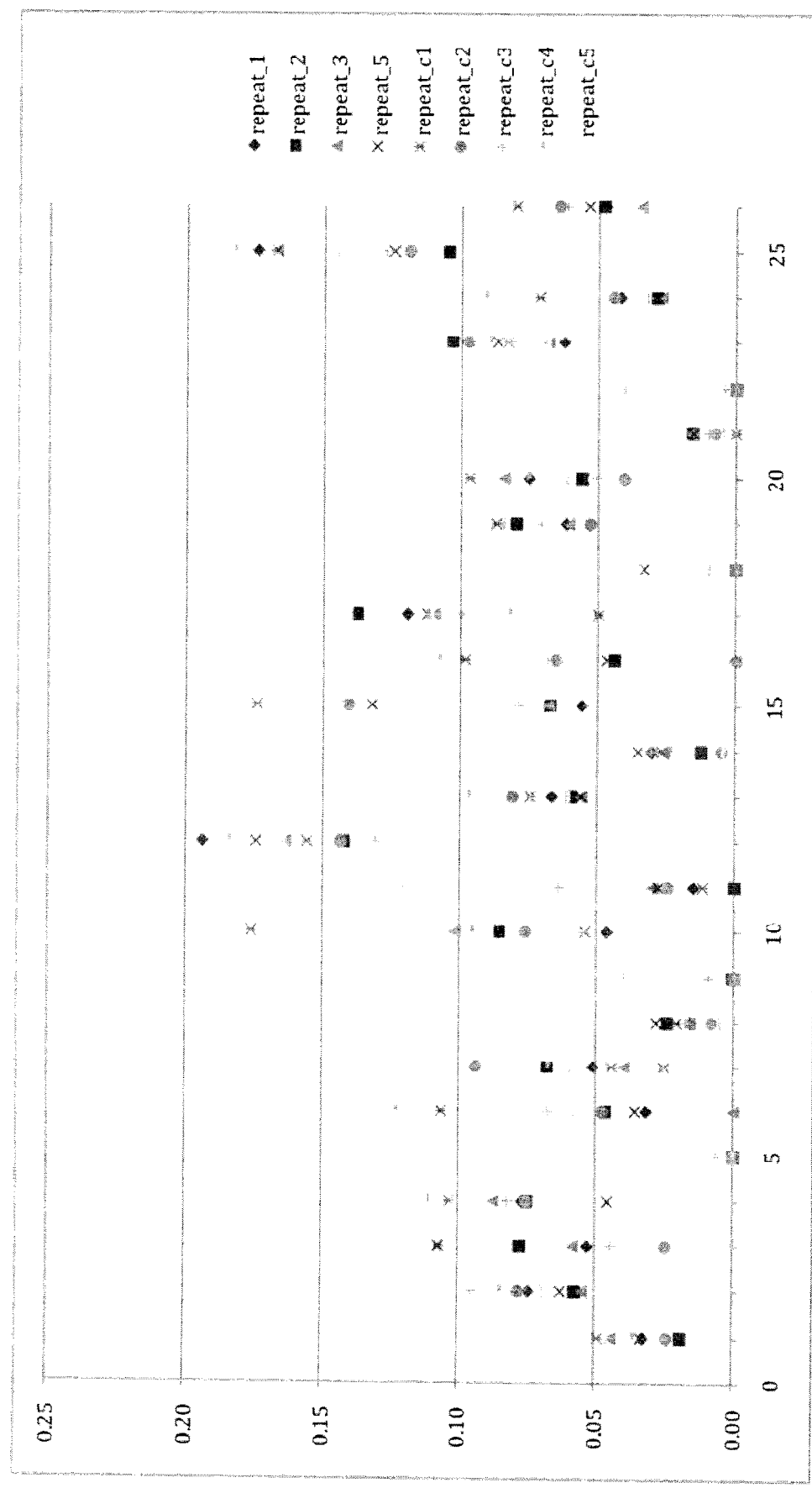
FIG. 10 shows CCSD_receptor values calculated using a damping factor with a damping parameter value of 25, according to Example 5. The y-axis is CCSD_receptor and the x-axis is the residue index as described in Table 7.
Figure 11:
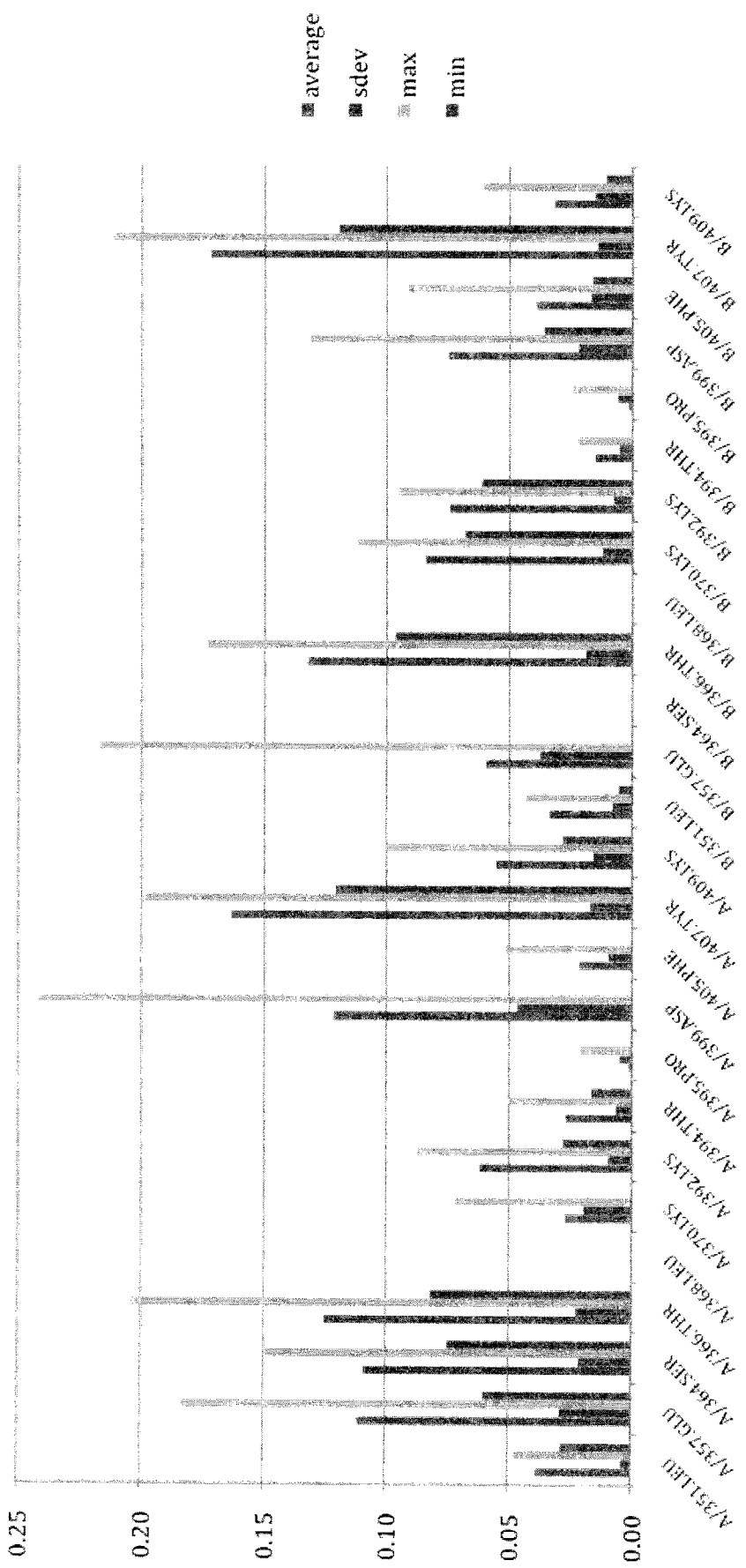
FIG. 11 shows backrub trajectory analysis of the repeat_1 IR run with alpha-damping=0. The y-axis is CCSD_receptor, and the x axis is the analyzed residue. For each residue, the leftmost bar is the average, the center left bar is the standard deviation, the center right bar is the maximum value and the rightmost bar is the minimum value.
Figure 12:
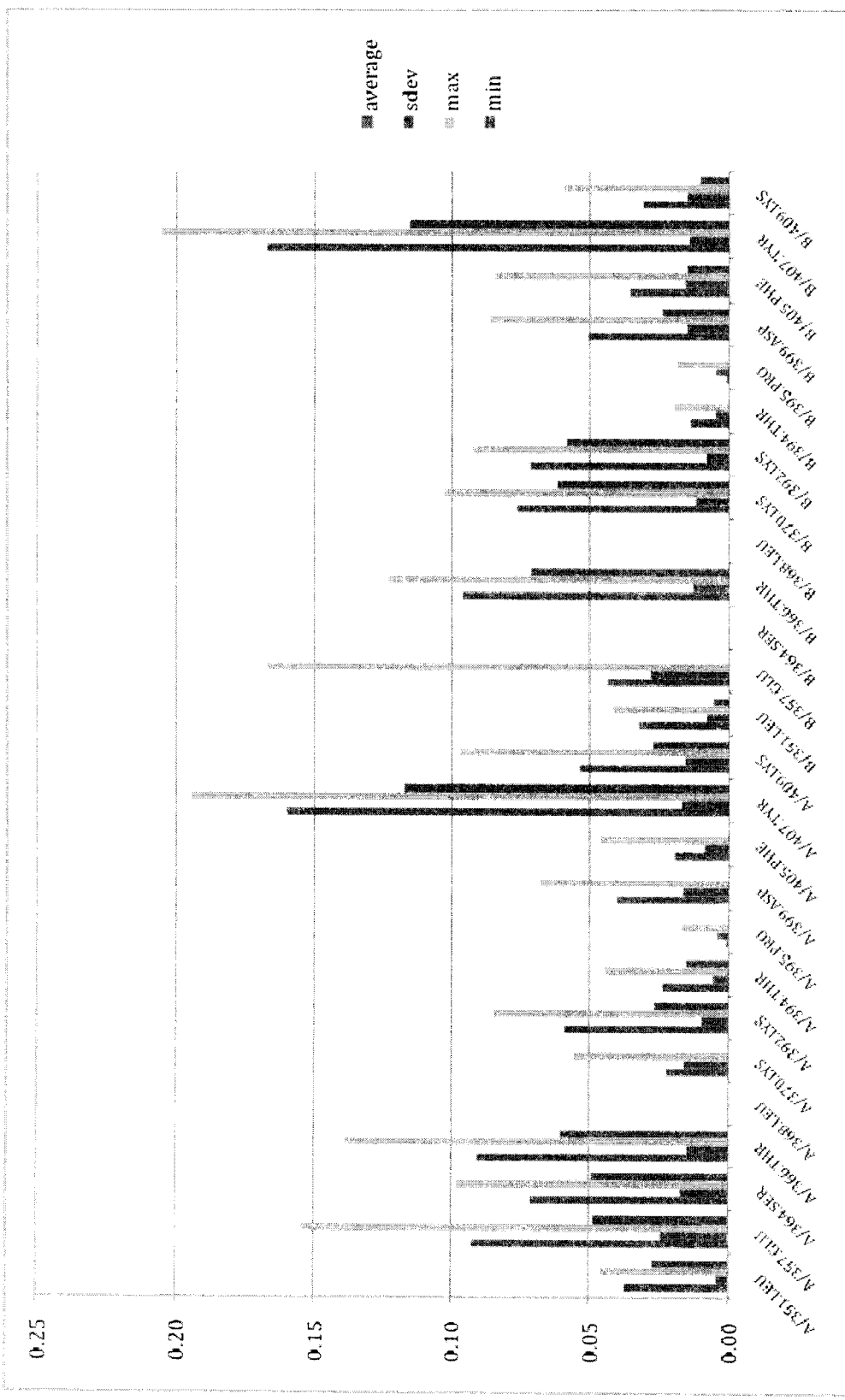
FIG. 12 shows backrub trajectory analysis of the repeat_1 IR run with alpha-damping=25. The y-axis is CCSD_receptor, and the x axis is the analyzed residue. For each residue, the leftmost bar is the average, the center left bar is the standard deviation, the center right bar is the maximum value and the rightmost bar is the minimum value.
Figure 13:
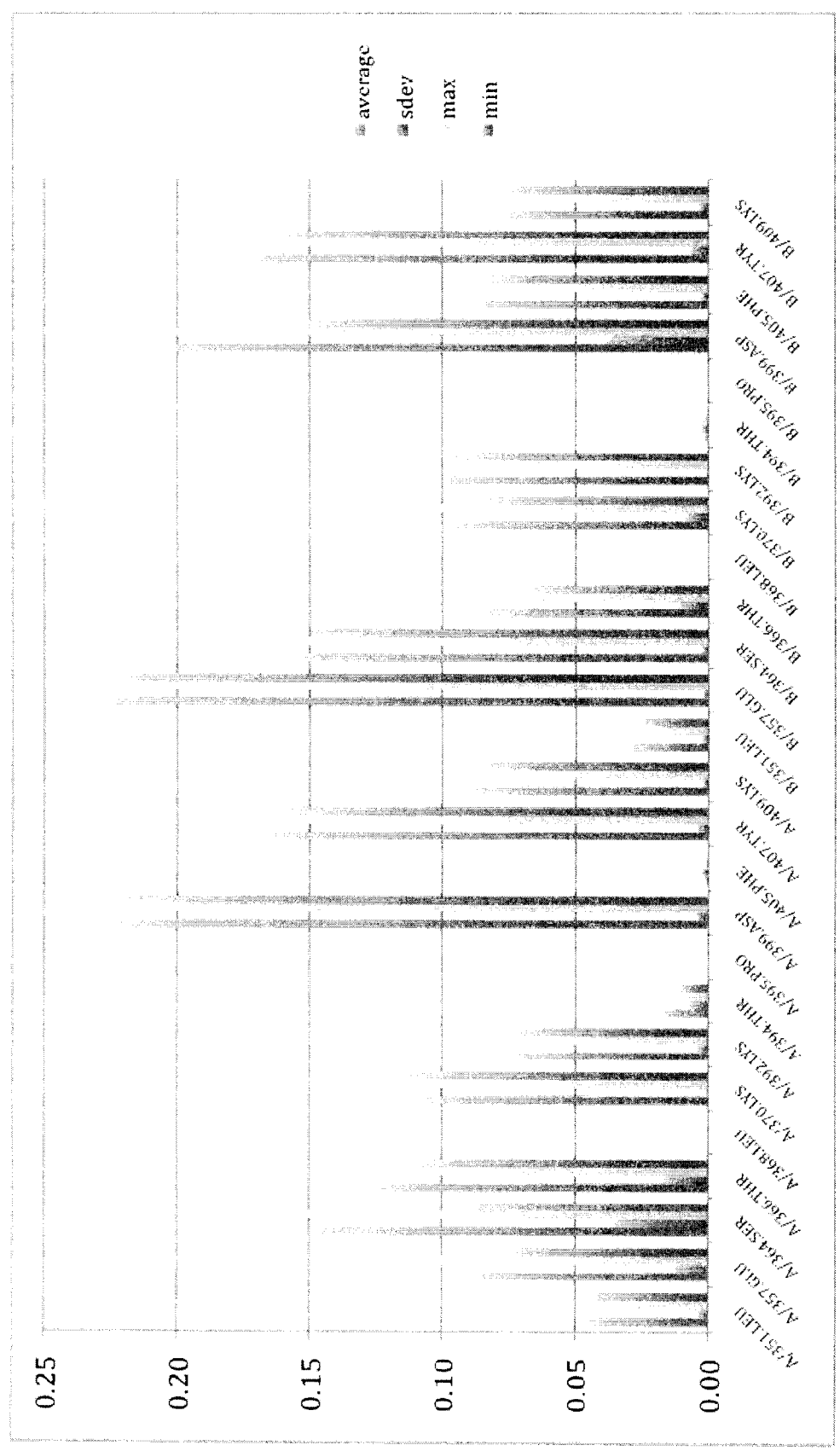
FIG. 13 shows backrub trajectory analysis of a run based on short backbone conformational sampling using a local random-walk with alpha-damping=0. The y-axis is CCSD_receptor, and the x axis is the analyzed residue. For each residue, the leftmost bar is the average, the center left bar is the standard deviation, the center right bar is the maximum value and the rightmost bar is the minimum value.
Figure 14:
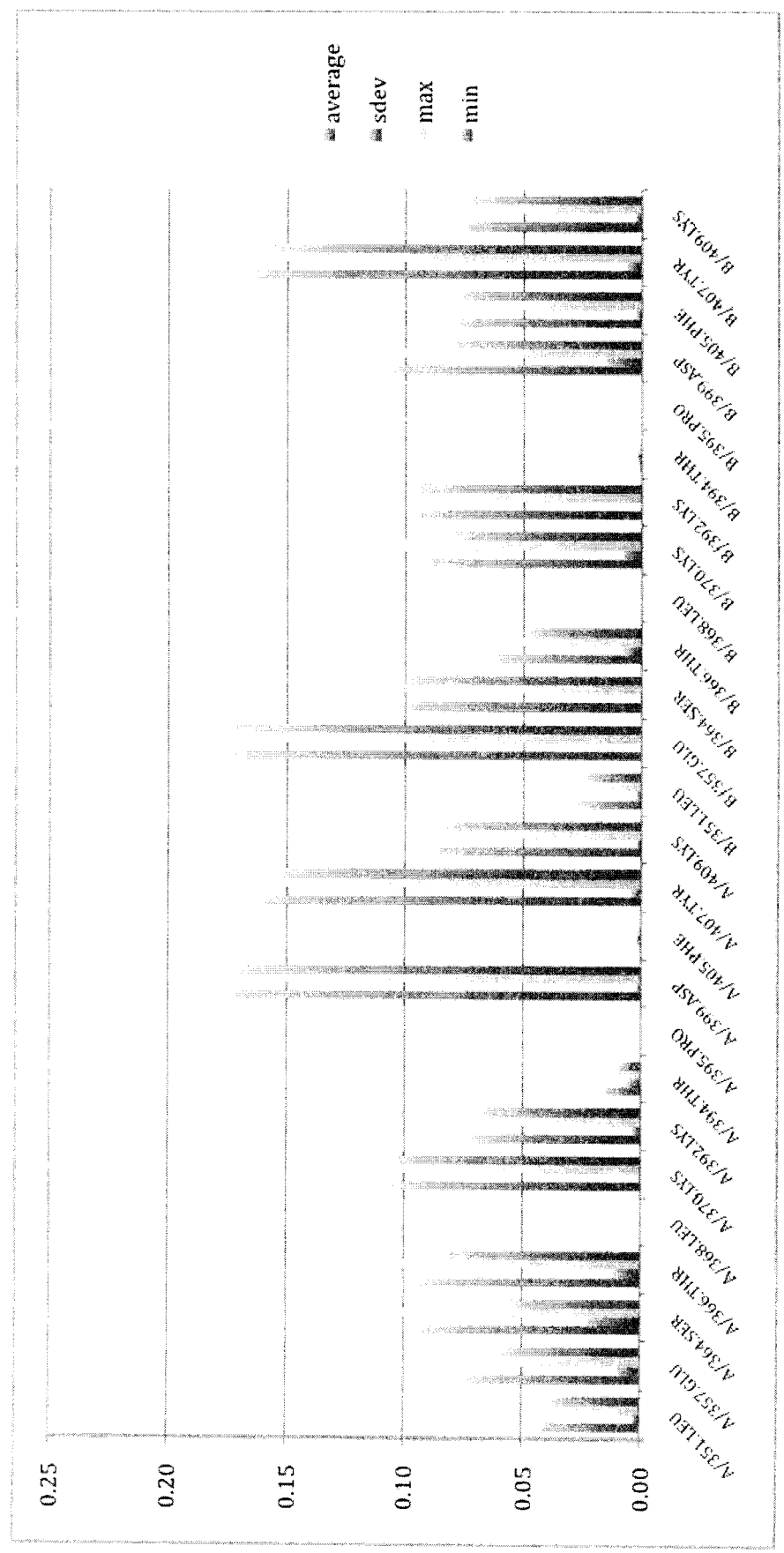
FIG. 14 shows backrub trajectory analysis of a run based on short backbone conformational sampling using a local random-walk with alpha-damping=25. The y-axis is CCSD_receptor, and the x axis is the analyzed residue. For each residue, the leftmost bar is the average, the center left bar is the standard deviation, the center right bar is the maximum value and the rightmost bar is the minimum value.
Figure 15:
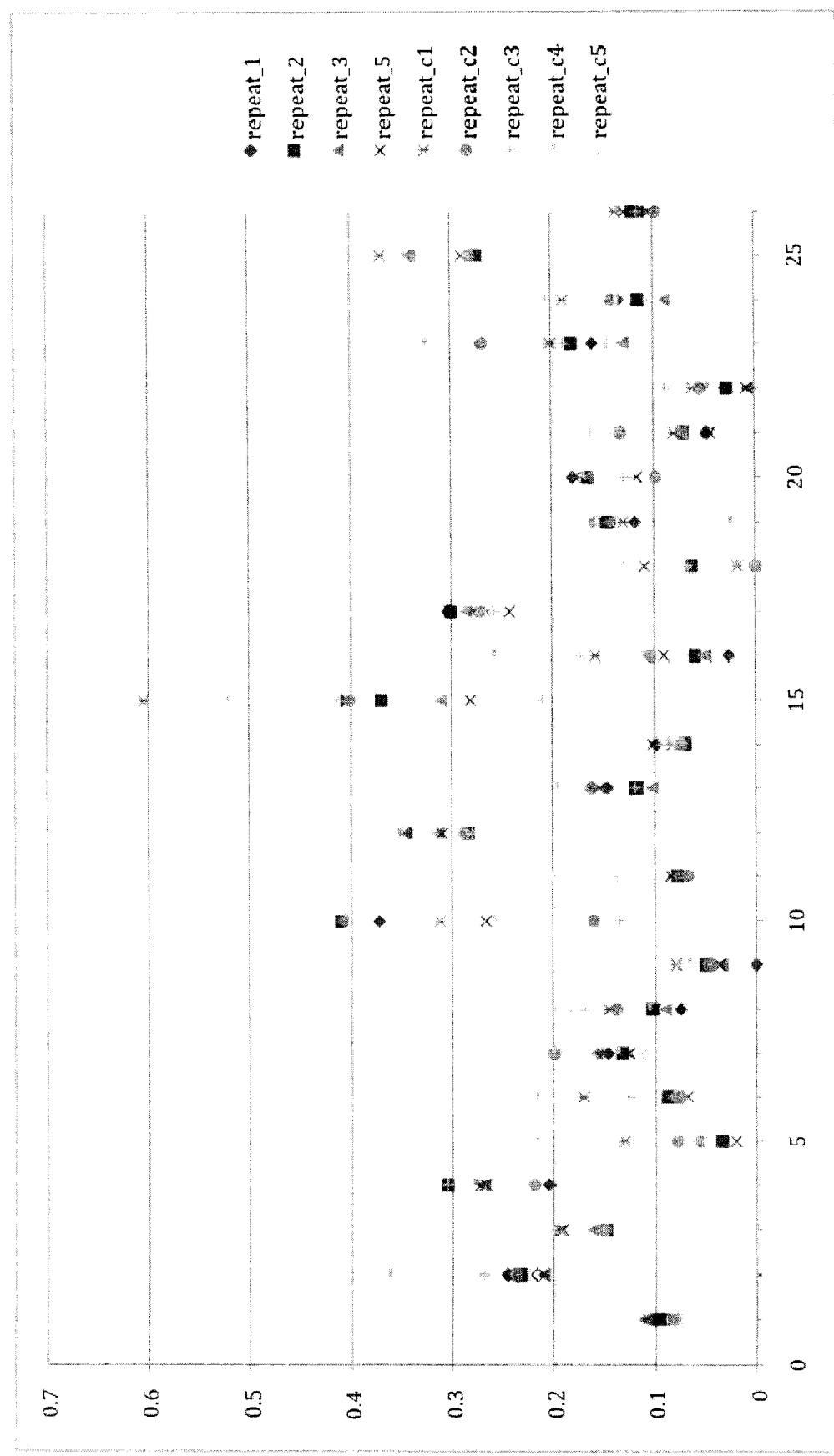
FIG. 15 shows CCSD_receptor values for close-cutoff=4.0 and alpha-damping=0. The y-axis is CCSD_receptor, the x-axis is the residue index as described in Table 7.
Figure 16:
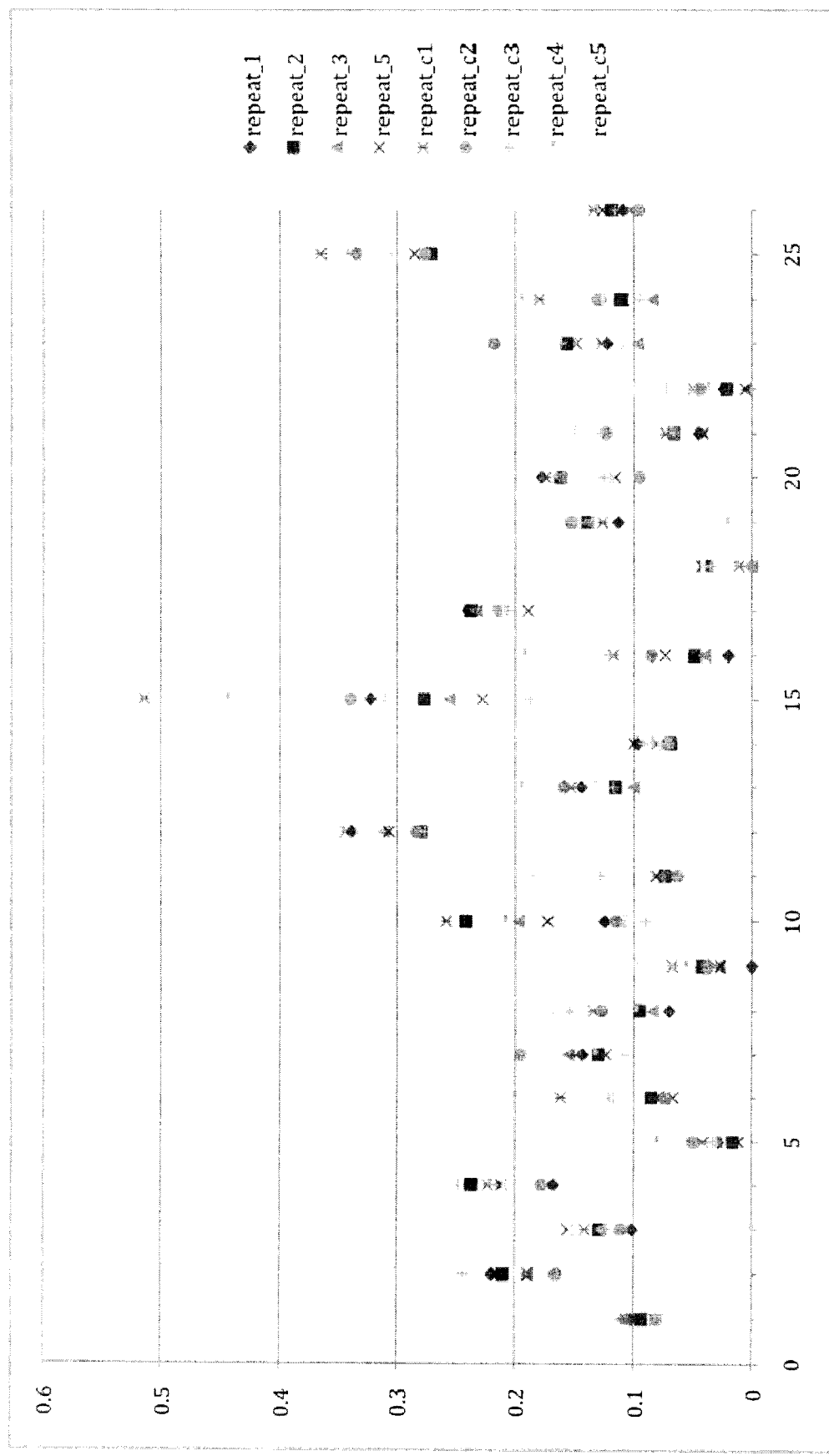
FIG. 16 shows CCSD_receptor values for close-cutoff=4.0 and alpha-damping=15. The y-axis is CCSD_receptor, the x-axis is the residue index as described in Table 7.
Figure 17:
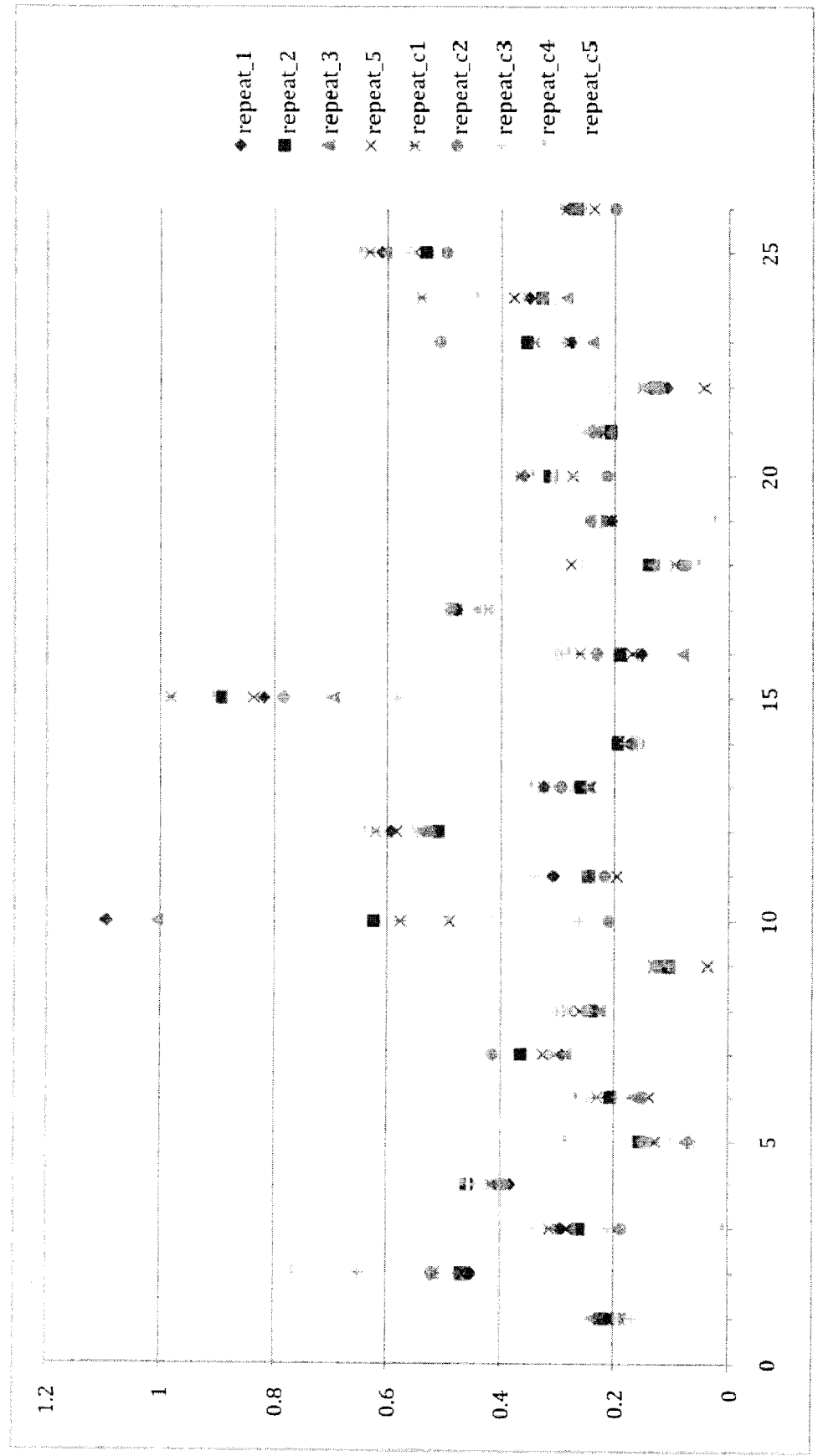
FIG. 17 shows CCSD_receptor values for close-cutoff=4.5 and alpha-damping=0. The y-axis is CCSD_receptor, the x-axis is the residue index as described in Table 7.
Figure 18:
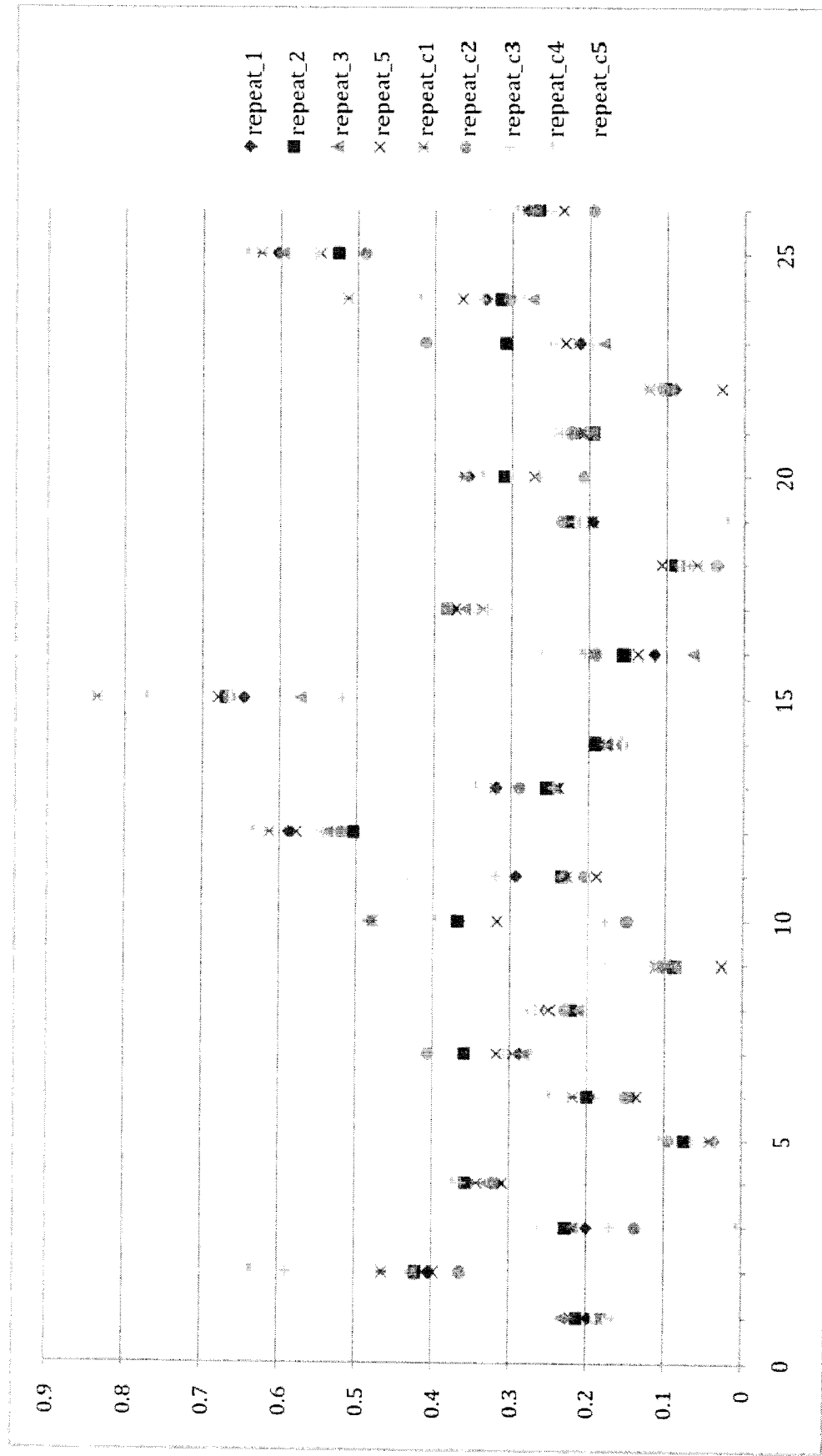
FIG. 18 shows CCSD_receptor values for close-cutoff=4.5 and alpha-damping=15. The y-axis is CCSD_receptor, the x-axis is the residue index as described in Table 7.

FIGS. 8, 9 and 10 show CCSD_receptor values calculated using a damping factor with damping parameter values of 0, 15 and 25, respectively. The damping factor shows clear improvement over data without damping. As expected, buried interface residues with low buried_sasa (364, 357, 368, (399)) show reduced variation. CCSD_receptor values for residues with low buried_sasa are overall reduced with increasing damping factor. The proposed best damping value is 20-25. At this value, the data shows clear reduction in outliers with high CCSD values and the lowered CCSD values for some of the smaller residues is tolerated because the importance for affinity is questionable. Importantly, the high scoring hotspots (407) are not affected by the damping factor.

TABLE 7

Residue selection in CH3CH3 interface

| res index | residue | relevance/characteristic |
|---|---|---|
| 1 | A/351.LEU | buried, 0.32 rel.bsa, important for packing - protection of hydophobic core |
| 2 | A/357.GLU | buried, variable packing, sidechain bends in - making variable inter- and intra-chain contacts |
| 3 | A/364.SER | mainly buried, not important for binding |
| 4 | A/366.THR | buried, hotspot and hydrophobic core of interface |
| 5 | A/368.LEU | buried, but facing cavity, hotspot - important for packing - protection of hydophobic core |
| 6 | A/370.LYS | partially buried, variable |
| 7 | A/392.LYS | solvant accessibly, variable |
| 8 | A/394.THR | buried, 0.32 rel.bas, important for packing - protection of hydophobic core |
| 9 | A/395.PRO | solvant accessibly, important for packing |
| 10 | A/399.ASP | partially solvant accessibly, important salt bridge with 409 |
| 11 | A/405.PHE | buried, hotspot, important for packing - protection of hydophobic core |
| 12 | A/407.TYR | buried, hotspot and hydrophobic core of interface |
| 13 | A/409.LYS | mainly buried, hotspot, important for packing - protection of hydophobic core and salt bridge to 399 |
| 14 | B/351.LEU | buried, 0.32 rel.bsa, important for packing - protection of hydophobic core |
| 15 | B/357.GLU | buried, variable packing, sidechain bends in - making variable inter- and intra-chain contacts |
| 16 | B/364.SER | mainly buried, not important for binding |
| 17 | B/366.THR | buried, hotspot and hydrophobic core of interface |
| 18 | B/368.LEU | buried, but facing cavity, hotspot - important for packing -protection of hydophobic core |
| 19 | B/370.LYS | partially buried, variable |
| 20 | B/392.LYS | solvant accessibly, variable |
| 21 | B/394.THR | buried, 0.32 rel.bas, important for packing - protection of hydophobic core |
| 22 | B/395.PRO | solvant accessibly, important for packing |
| 23 | B/399.ASP | partially solvant accessibly, important salt bridge with 409 |
| 24 | B/405.PHE | buried, hotspot, important for packing - protection of hydophobic core |
| 25 | B/407.TYR | buried, hotspot and hydrophobic core of interface |
| 26 | B/409.LYS | mainly buried, hotspot, important for packing - protection of hydophobic core and salt bridge to 399 |

Example 6

Analysis of CCSD_receptor Variation on Backrub Trajectories

Backrub trajectories of two ensembles of structures were analyzed using two damping parameters 0 and 25. The ensemble of structures were obtained from (a) about one hundred snapshots from the random walk used to produce the model of Repeat_1 above; and (b) five snapshots obtained from a short backbone conformational sampling using a random-walk local to the residue positions in the vicinity of positions A/366, A/392, A/394, B/351, B/368, B/397, B/405 and B/407 in the CH3 domain of the Fc:FcR.

The results of this analysis are shown in FIGS. 11-14. The alpha-damping factors 20 and 25 had showed a clear improvement and the analysis of the IR repack backrub trajectory was similar to the analysis of the individual repacks. The backrub trajectory of the packing-workflow identity repack on the other hand shows very little variation in the CCSD values. The alpha-damping factor can scale the CCSD values, but some of the artifacts are likely due to the packing-workflow/backrub itself.

Example 7

Analysis of CCSD_receptor Variation With Variation of Close-Cutoff=3.6, 4.0, 4.5 and Alpha-Damping=0,15 on Individual IR Models CCSDs for the receptor were obtained using varied cutoff values and damping parameters. For damping parameters of 0 and 15, results using a cutoff value of 3.6 Å are shown in FIGS. 8 and 9, while results for cutoff values of 4.0 and 4.5 Å are shown in FIGS. 15-18. Independent of the cutoff distance, the overall CCSD profile is very similar. The increased cutoff of >4.0 Å together with the alpha-damping improves predictability without losing the information of the 3.6 Å cutoff data. Exponential damping reduces problems with artificially high variance, and a value in the range 20-25 seems optimal. The CCSD does not show any significant differences between a 3.6 and 4.0 A distance cut-off. Based on that alone, it is unclear if there is any additional benefit in having multiple CCSD computations with different cut-offs.

Some of the variation that is observed in the CCSD is true variation, given that the structure is very flexible at that point. CCSD is not designed to be that coarse-grained to be invariant to these significant structural variations, hence it will display variation as well. The problem is that structurally flexible regions of the proteins are not properly modeled as such in the short backrub trajectory in the packing workflow. This is hence not a problem with the CCSD metric per se.

The articles "a", "an" and "the" as used herein do not exclude a plural number of the referent, unless context clearly dictates otherwise. The conjunction "or" is not mutually exclusive, unless context clearly dictates otherwise. The term "include" is used to refer to non-exhaustive examples.

All references, publications, patent applications, issued patents, accession records and databases cited herein, including in any appendices, are incorporated by reference in their entirety for all purposes.

I claim:

1. A method of engineering a variant protein relative to a parent protein, the parent protein comprising a first residue comprising one or more residue atoms, the method comprising:

(a) calculating a summation of one or more close contact potentials of the parent protein based on respective distances between the one or more residue atoms of the first residue of the parent protein and one or more environment atoms of the one or more residue atoms of the first residue of the parent protein, in accordance with a close contact potential formula of the form:

$$U_{ab}(r_{ab}) = \begin{cases} 1 & \text{if } r_{ab} < r_c \\ \frac{1}{d}(r_c - r_{ab}) & \text{if } r_c < r_{ab} < r_c + d \\ 0 & \text{if } r_{ab} < r_c + d \\ 0 & \text{if } \beta \end{cases}$$

wherein, $U_{ab}(r_{ab})$ is the close contact potential between a residue atom a of the first residue and an environmental atom b, d is a non-zero offset, $r_c$, is equal to or greater than a first distance threshold, $r_{ab}$ is the distance between a residue atom a of the first residue and an environmental atom b, β refers to atoms a and b that are either members of the same residue or that are bonded either directly (1-2 bonded), through one intervening atom (1-3 bonded) or through two intervening atoms (1-4 bonded), (b) using a computer system to calculate a first contact area of the one or more residue atoms of the first residue of the parent protein that are exposed to the one or more environment atoms as a difference between (i) a total solvent accessible surface area of the one or more residue atoms of the first residue of the parent protein and (ii) a solvent accessible area of the one or more residue atoms of the first residue of the parent protein in the presence of the parent protein, wherein the method further comprises calculating the total solvent accessible surface area of the one or more residue atoms of the first residue of the parent protein and calculating the solvent accessible area of the one or more residue atoms of the first residue of the parent protein in the presence of the parent protein using the computer system, (c) calculating a first close contact surface density (CCSD) by dividing the summation of the one or more close contact potentials of the parent protein by the first contact area, (d) mutating in silico one or more residues of the first protein to provide the variant protein, (e) calculating a summation of one or more close contact potentials of the variant protein based on respective distances between the one or more residue atoms of the first residue of the variant protein and one or more environment atoms of the one or more residue atoms of the first residue of the variant protein in accordance with the close contact potential formula of the calculating (a), (f) calculating a second contact area of the one or more residue atoms of the first residue of the variant protein that are exposed to the one or more environment atoms as a difference between (i) a total solvent accessible surface area of the one or more residue atoms of the first residue of the variant protein and (ii) the solvent accessible area of the one or more residue atoms of the first residue of the variant protein in the presence of the variant protein, (g) calculating a second CCSD by dividing the summation of the one or more close contact potentials of the variant protein by the second contact area, (h) confirming the variant protein has improved stability relative to the parent protein by comparing the second CCSD to the first CCSD; and (i) making the variant protein, wherein the variant protein is other than a wild-type protein.

2. The method of claim 1 further comprising normalizing the first CCSD prior to the calculating (c).

3. (Withdrawn, Previously Presented) The method of claim 1 wherein the first contact area is greater than about 10 Å$^2$.

4. The method of claim 1 wherein the first CCSD is less than about 0.25 Å$^{-2}$.

5. The method of claim 1 further comprising damping the first CCSD.

6. The method of claim 1 wherein the parent protein is bound to a molecule to form a complex.

7. The method of claim 6 wherein the molecule is a second protein.

8. The method of claim 7 wherein the parent protein is a ligand and the second protein is a receptor, or wherein the parent protein is a receptor and the second protein is a ligand.

9. The method of claim 8 wherein the one or more environment atoms of the one or more residue atoms of the first residue of the parent protein are selected from one or more ligand atoms and one or more receptor atoms.

* * * * *